(12) United States Patent
Kasai

(10) Patent No.: US 7,280,283 B1
(45) Date of Patent: Oct. 9, 2007

(54) ENDOSCOPIC OBJECTIVE OPTICAL SYSTEM, AND IMAGING SYSTEM USING THE SAME

(75) Inventor: Ken Kasai, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/434,793

(22) Filed: May 17, 2006

(51) Int. Cl.
*G02B 21/02* (2006.01)
(52) U.S. Cl. .................................... 359/656
(58) Field of Classification Search ......... 359/656–661
See application file for complete search history.

(56) References Cited

U.S. PATENT DOCUMENTS 6,464,631 B1   10/2002   Girke et al.

FOREIGN PATENT DOCUMENTS

JP   60-080816   5/1985

*Primary Examiner*—Scott J. Sugarman
*Assistant Examiner*—Darryl J. Collins
(74) *Attorney, Agent, or Firm*—Kenyon & Kenyon LLP

(57) ABSTRACT

The invention provides a wide-angle, low-cost endoscopic objective optical system that is reduced in terms of distortion and field curvature and composed only of spherical lenses, especially a video endoscopic objective optical system. The optical system comprises a first group G1 comprising a negative meniscus lens convex on an object side thereof, an aperture stop S, a second group G2 comprising a positive lens having a plane directed toward an object point side, a third group G3 including at least one concave refractive surface and having a positive refracting power as a whole, and a fourth group G4 comprising a cemented lens comprising a negative meniscus lens and a double-convex lens and having positive refracting power, so that an image is formed at an imaging device I via the first group G1 to the fourth group G4. A chief ray is reflected at the convex surface of the positive lens in the second group in a direction away from an optical axis.

23 Claims, 32 Drawing Sheets

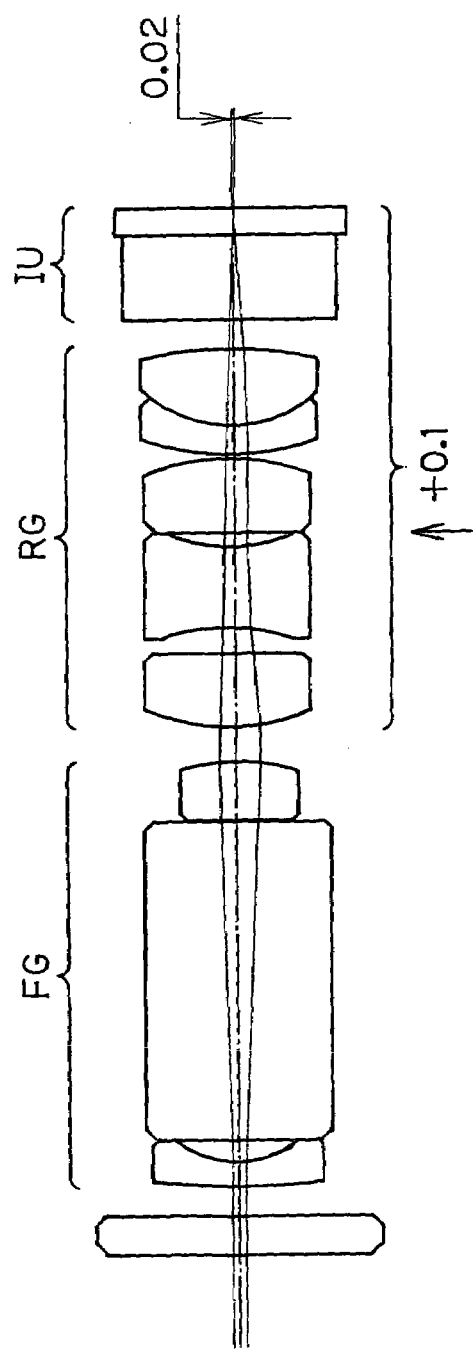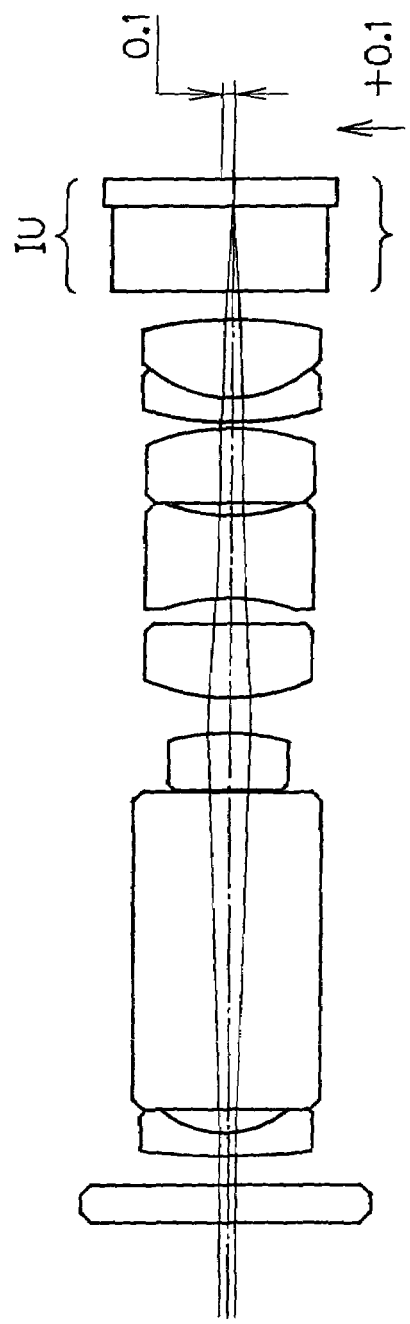
FIG. 9(a)
FIG. 9(b)

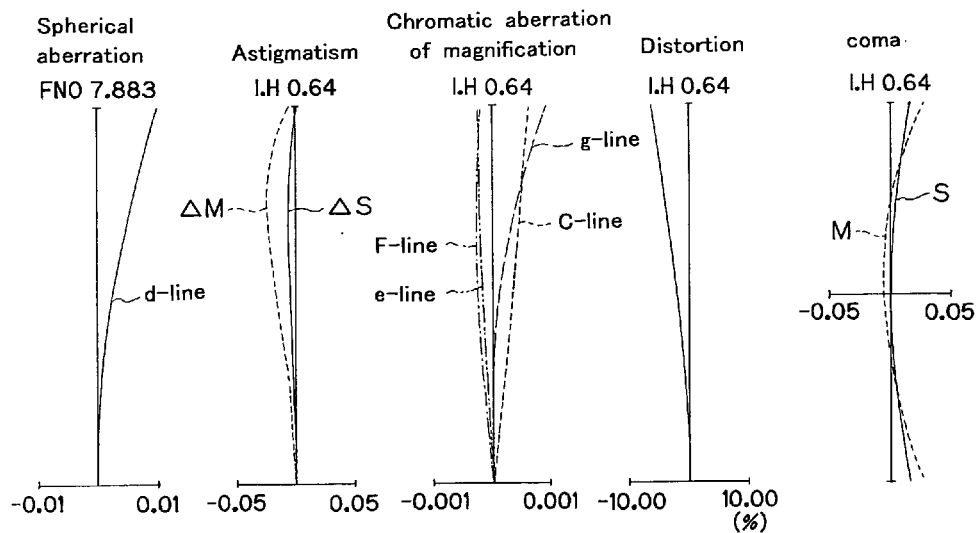
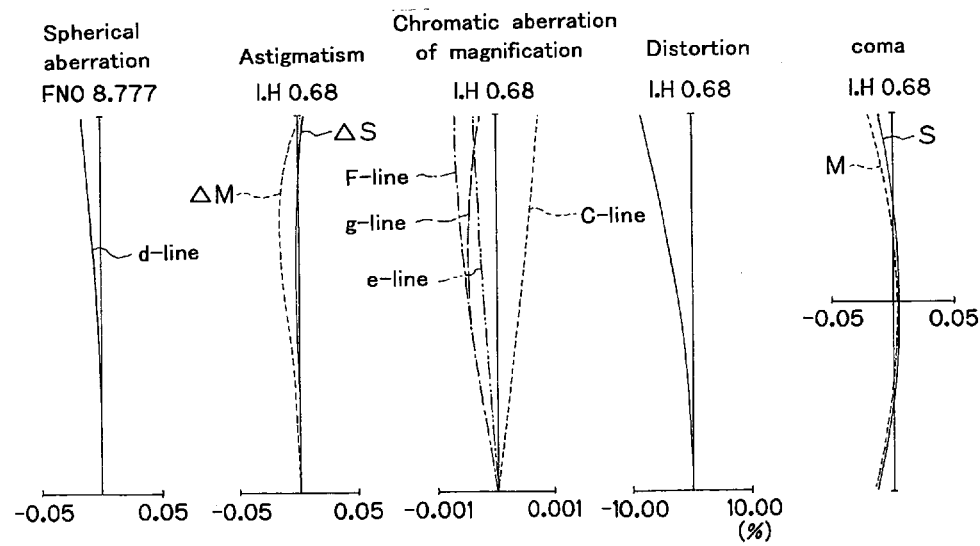

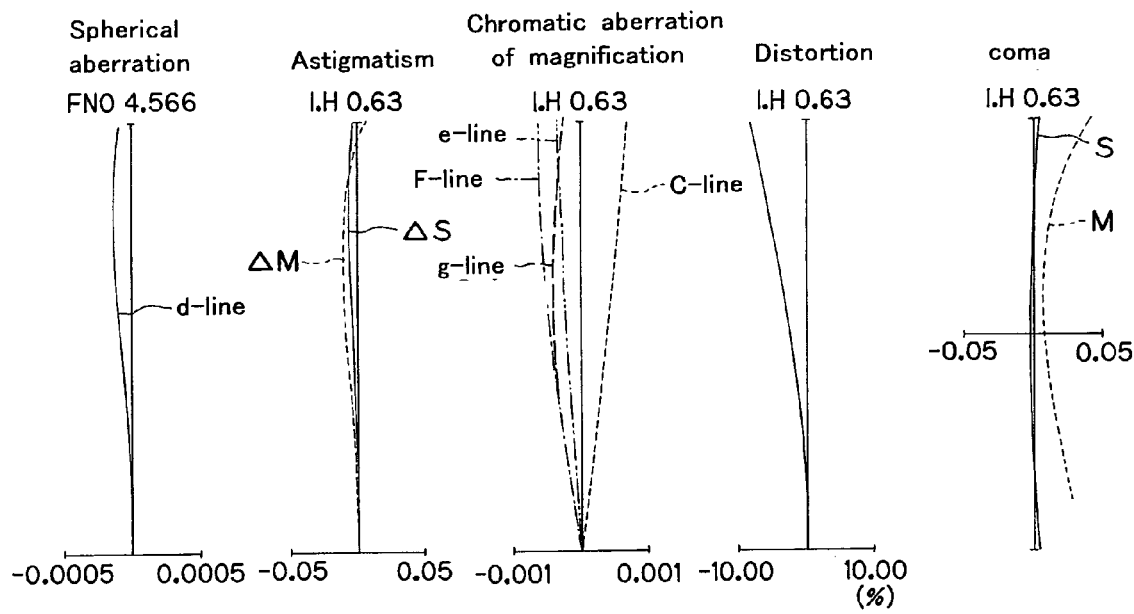
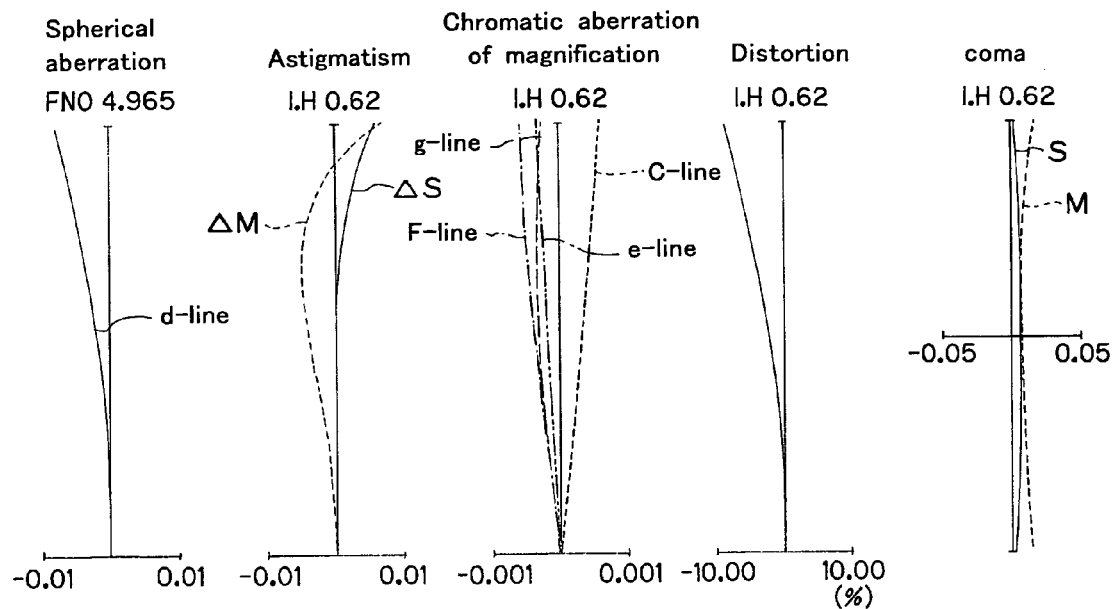

FIG. 41(a)  FIG. 41(b)
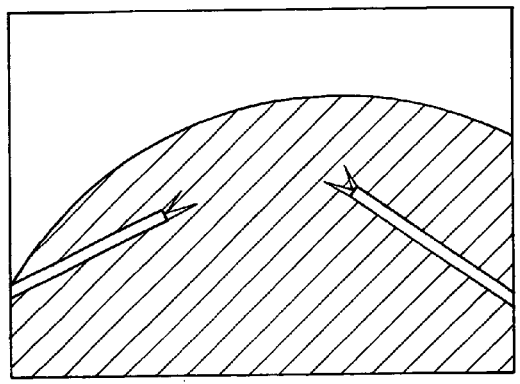 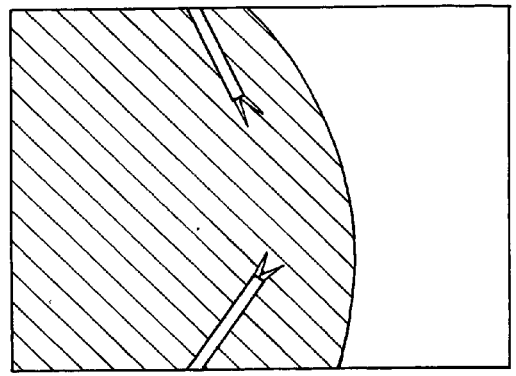
FIG. 42(a)  FIG. 42(b)  FIG. 42(c)
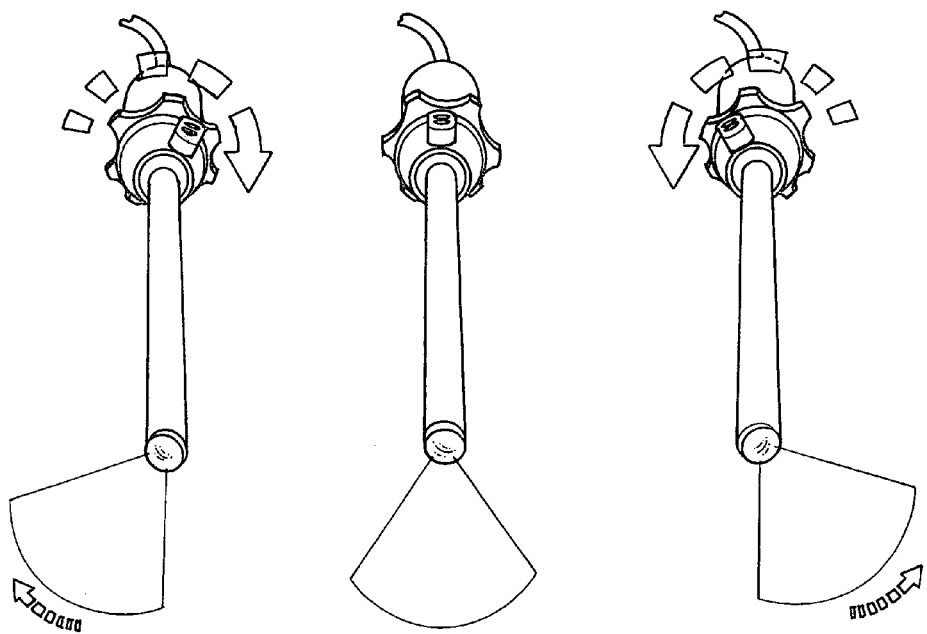

ENDOSCOPIC OBJECTIVE OPTICAL SYSTEM, AND IMAGING SYSTEM USING THE SAME

BACKGROUND OF THE INVENTION

The present invention relates generally to an endoscopic objective optical system, and an imaging system using the same, and more particularly to a video endoscopic objective optical system and an electronic endoscope.

For endoscopes, especially those used in medical fields, it is desired to have a wide-angle, wide-field arrangement for the purposes of ensuring ready detection of affected sites in the body cavity, treatment of lesions without oversight, etc. When the endoscopes are used through the abdominal cavity, they need have an angle of field of at least about 70°.

To enhance relay efficiency, an endoscopic optical system is desirously of the telecentric type adapted to allow chief rays to be vertically incident on image relay means. A wide-angle telecentric optical system is achieved by use of a retrofocus optical system made up of a front unit of negative power, a stop and a rear unit of positive power, with the position of the stop in alignment with the front focal position of the rear unit. Basically, however, that telecentric optical system has the nature of producing a lot more negative distortion, because negative distortion occurs through negative refracting power before the stop, and more because negative distortion occurs through positive refracting power after the stop.

Increased distortion is inconvenient and un-preferable for an operator, because there is a great deal of alienation between a real object and an image.

As means for cutting down distortion, Patent Publication 1 shows an endoscopic objective lens of the retrofocus type with less distortion, in which the front unit is constructed of a positive lens and one negative meniscus lens, as depicted in the sectional view attached hereto as FIG. 37.

Further, Patent Publication 2 shows a technique of correcting distortion by use of an aspheric lens.

Furthermore, Patent Publication 3 shows a technique of holding back the occurrence of distortion with no use of any aspheric lens.

With the teachings of Patent Publication 1, however, the convex lens placed on the object side is located nearer to the object side than the concave lens or the distance between them is longer than its distance with the stop, and light rays gain height under the action of the concave lens in the front unit, leading inevitably to an increased outer diameter. The endoscope is an insert; in other words, an increased outer diameter of the optical system attached to its distal portion is not preferable, because of rendering the insert portion huge.

On the other hand, Patent Publication 4 sets forth an example of a hard endoscopic objective optical system with field curvature overcorrected in a positive direction. When a relay lens is used as image relay means, it is known to produce positive field curvature at an objective lens located nearer to an object side with respect to the relay lens, thereby canceling out negative field curvature occurring at the relay lens. Patent Publication 4 is typical of such an objective optical system, as depicted in the astigmatism aberration diagram attached hereto as FIG. 38 (Patent Publication 4, FIG. 6). Nowhere in Patent Publication 4, however, is there any optical system disclosed, wherein an image must be formed on a plane as is the case with a video scope adapted to form an image on a CCD or other solid-state imaging device, and a fiber scope using an image guide, etc.

Further, the type using an aspheric lens as set forth in Patent Publication 2 has some considerable effect on removal of distortion; however, a problem with it is that the fabrication of aspheric lenses generally costs much.

Furthermore, the optical system shown in Patent Publication 3 uses a plurality of lenses for the front unit, and this is again not preferable because of a bit more lenses count leading to increased costs.

Such objective optical systems with reduced distortion and field curvature as described above are suitable for surgical operations under endoscopes. An endoscopic surgery involves making a small bore in the body cavity, and inserting forceps, etc. through the bore for surgery and treatment with a video scope, etc. inserted through the body cavity for getting hold of the field, and has the merit of being lesser invasive than an abdominal operation, finding applications primarily for removal of the gallbladder, surgical removal of the lung in the case of spontaneous pneumothorax, etc.

In the endoscopic surgery, the operator conducts operation while watching a video image on a TV monitor rather than watching directly the affected site, and so images with reduced distortion and field curvature are preferable because they apply no burdens on the operator. For endoscopic surgical operations, a hard video scope of good insert capability is commonly used, and an oblique-vision optical system with the direction of field set obliquely to the front with respect to its longitudinal direction is preferable for use with it. In the oblique-vision optical system, too, there is a need for the operator to easily gain the operating field. FIG. 39 is illustrative of the outward appearance of such a scope (hard endoscope). With an manipulation knob K rotated for instance 90° as indicated by an arrow, the field will turn on a monitor from the before-rotation state of FIG. 40(a) to the after-rotation state of FIG. 40(b).

FIG. 41(a) is illustrative of images on a monitor under endoscopic surgery. As a scope is rotated in its entirety, the image is flipped over with the top and bottom not in alignment with the gravity direction, as can be seen from FIG. 41(b); that is, on the monitor, the top and bottom will be no in alignment with a direction in which biopsy forceps manipulated by the operator appear. This will render endoscopic surgical operations needing meticulous manipulations very awkward.

To overcome such problems, Patent Publication 5 shows a technique of allowing a video scope itself to have a rotating function of turning the field direction without changing the top-and-bottom direction of an operator, as can be seen from FIGS. 42(a) to (c). Specifically, this publication discloses a technique of correcting image rotation by rotation of an image pickup plane 9 of an optical system, as shown in FIG. 43 (Patent Publication 5, FIG. 1).

With a structure, as in Patent Publication 5, of a CCD image pickup plane 9 integrally fixed to the end of a shaft 11 for rotation, however, there is a so-called "play" from errors of internal parts upon fabrication and clearances between parts. As the shaft 11 is rotated, therefore, the center of the field on a monitor makes movement just as in an arc orbit, as depicted in FIG. 44, rendering observation much hard.

Patent Publication 1
JP(A)60-80816
Patent Publication 2
U.S. Pat. No. 4,867,546
Patent Publication 3
U.S. Pat. No. 6,618,207
Patent Publication 4
JP (B) 5-85884

Patent Publication 5
U.S. Pat. No. 6,464,631

SUMMARY OF THE INVENTION

Such being the prior art, one object of the invention is to provide a wide-angle, low-cost endoscopic objective optical system, especially a video endoscopic objective optical system that is much more reduced in distortion and field curvature and composed only of spherical lenses.

Another object of the invention is to provide an oblique-vision optical system capable of turning the field direction to a desired direction with respect to the longitudinal direction of an endoscope, wherein even with the field direction rotated and turned, the occurrence of decentration at the center of the field on an viewing plane can be minimize, as well as an imaging system well fit for viewing on a TV monitor, for instance, an electronic endoscope.

According to one aspect of the invention, these objects are accomplishable by the provision of an endoscopic objective optical system adapted to capture an object image to form the object image at image relay means, characterized by comprising a front unit before, and a rear unit after, a substantially afocal portion, wherein said objective optical system is relatively rotatable with said front unit and said rear unit integral with said image relay means.

According to another aspect of the invention, there is provided an endoscopic objective optical system comprising, in order from an object side thereof, a first group comprising a negative meniscus lens convex on an object side thereof, an aperture stop, a second group comprising a positive lens having a plane directed toward an object point side, a third group including at least one concave refractive surface and having a positive refracting power as a whole, and a fourth group comprising a cemented lens comprising a negative meniscus lens and a double-convex lens and having positive refracting power, so that an image is formed at an imaging device via said first group to said fourth group, characterized in that a chief ray is reflected at the convex surface of the positive lens in said second group in a direction away from an optical axis.

Preferably in this aspect of the invention, the following conditions should be satisfied:

$$2 < f_2(n_2-1)/t_2 < 6 \tag{1}$$

$$-2.3 < f_1/F < -0.9 \tag{2}$$

$$-0.6 < PS3 < -0.2 \tag{3}$$

$$vp > 50, vn < 30 \tag{4}$$

$$2.3 < f_4/F \tag{5}$$

where $t_2$, $f_2$ and $n_2$ is the thickness, focal length and refractive index of the positive lens in said second group, respectively, $f_1$ is the focal length of the negative meniscus lens in said first group, F is the focal length of the whole optical system, PS3 is a Petzval's sum due to the concave refractive surface in said third group, vp and vn are the d-line Abbe constants of the positive lens and negative lens in said fourth group, and $f_4$ is the focal length of said fourth group.

According to yet another aspect of the invention, there is provided an imaging system comprising any one of the foregoing endoscopic objective optical systems and a solid-state imaging device located on an image plane thereof, characterized in that a front unit is made up of said first group, said aperture stop and said second group, and a rear unit is made up of said third group and said fourth group, wherein said rear unit and said solid-state imaging device have a mechanically integrated structure in such a way as to be relatively rotatable with respect to said front unit with the longitudinal direction of the imaging device as an axis, and the angle of incidence of an axial marginal ray from said front unit on said rear unit is substantially parallel with said axis of rotation.

According to a further aspect of the invention, there is provided an imaging system comprising an endoscopic objective optical system comprising a front unit comprising, in order from an object side thereof, a negative lens, a stop and a positive lens and a rear unit having a positive refracting power as a whole and a solid-state imaging device located on an image plane thereof, characterized in that said rear unit and said solid-state imaging device have a mechanically integrated structure in such a way as to be rotatable with respect to said front unit with the longitudinal direction of the imaging system as an axis, and the angle of incidence of an axial marginal ray from said front unit on said rear unit is substantially parallel with said axis of rotation.

Preferably in each of the foregoing imaging systems, the following condition should be satisfied:

$$-0.3 < (f_2-|f_1|)/F < 1.5 \tag{6}$$

where $f_1$ is the focal length of the negative lens in said front unit, $f_2$ is the focal length of the positive lens in said front unit, and F is the focal length of the whole endoscopic objective optical system.

If a prism is used with the front unit of the endoscopic objective optical system, then an oblique-vision optical system can be set up.

The invention encompasses how to assemble such endoscopic objective optical systems and imaging systems as described above.

The invention as defined above can provide a wide-angle endoscopic objective optical system, especially a video endoscopic objective optical system, which is minimized in distortion and field curvature and made up of only a relatively fewer spherical lenses, and an oblique-vision optical system capable of rotating in such a way as to set the desired field direction with respect to the longitudinal direction of an endoscope. The invention can further provide an optical system that is minimized in terms of the occurrence of decentration at the center of the field on a viewing plane even when an endoscope is rotated to turn the field direction to the desired field, thereby achieving an electronic endoscope most fit for viewing on TV monitors.

Still other objects and advantages of the invention will in part be obvious and will in part be apparent from the specification.

The invention accordingly comprises the features of construction, combinations of elements, and arrangement of parts which will be exemplified in the construction hereinafter set forth, and the scope of the invention will be indicated in the claims.

BRIEF DESCRIPTION OF THE DRAWINGS

FIG. 9 is illustrative of a displacement of the center of an image with respect to the center of the field, which occurs when, in Example 5(a), and a prior art example (b), the movable part is shifted vertically to the optical axis.

FIG. 26 is an aberration diagram, as in FIG. 22, for the endoscopic objective optical system according to Example 5.

FIG. 27 is an aberration diagram, as in FIG. 22, for the endoscopic objective optical system according to Example 6.

FIG. 28 is an aberration diagram, as in FIG. 22, for the endoscopic objective optical system according to Example 7.

FIG. 29 is an aberration diagram, as in FIG. 22, for the endoscopic objective optical system according to Example 8.

FIG. 41 is illustrative of how a monitor image is observed before (a) and after (b) rotation under surgery using an endoscope.

FIG. 42 is illustrative of how the field direction of a video scope is turned.

DESCRIPTION OF THE PREFERRED EMBODIMENTS

The above arrangements of, and the requirements for, the inventive endoscopic objective optical system and the imaging system incorporating it are first explained.

When a retrofocus type is applied to an endoscopic objective optical system, one possible approach to correction of distortion is to locate a convex lens in front of a concave lens on an object point side; however, this would be impossible in consideration of outer diameter requirements. In the invention, therefore, importance is placed on a convex lens just after a stop. Imaging requires having relatively tight convex action near the stop; however, this would appear to induce tight negative curvature paraxially in general.

Figure 1A:
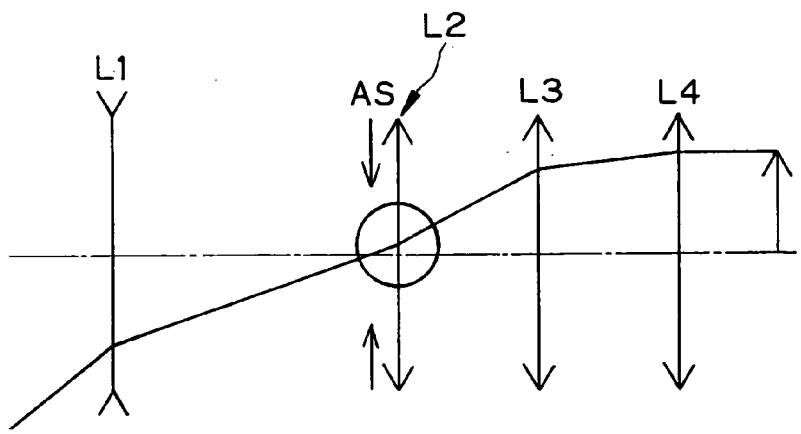
FIG. 1 is illustrative of the refraction of an off-axis chief ray through the inventive endoscopic objective optical system as well as through a prior art endoscopic objective optical system.
Figure 1B:
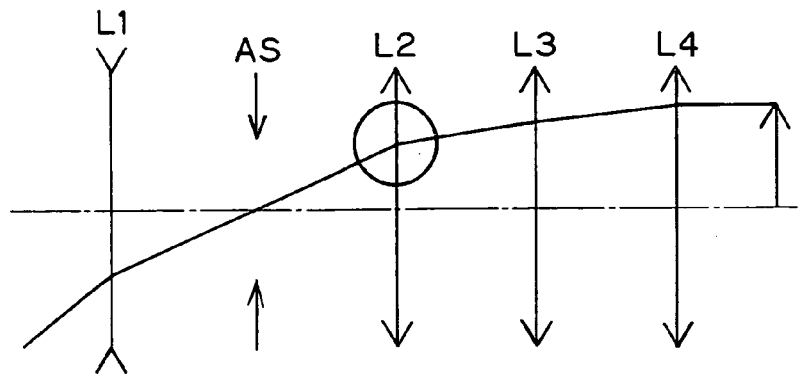
Figure 37:
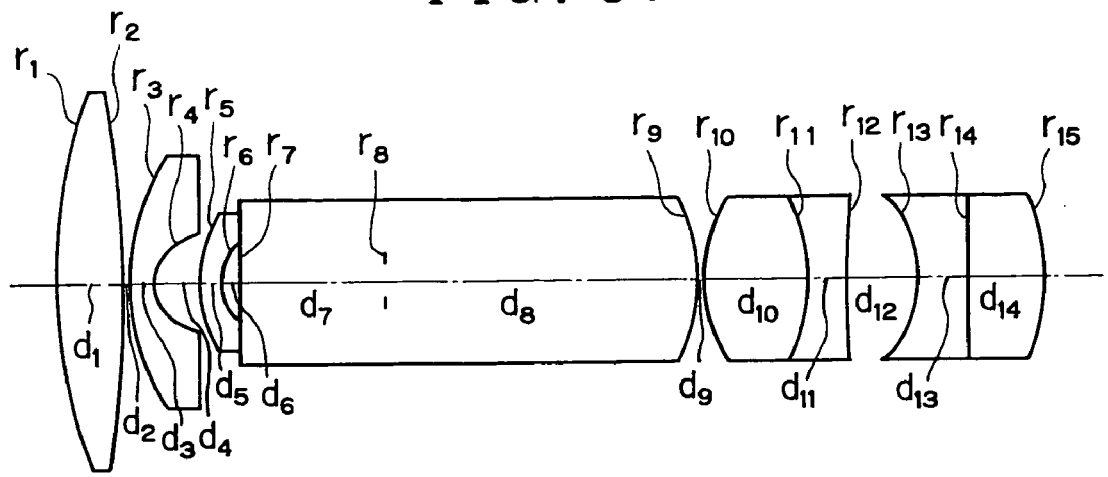
FIG. 37 is illustrative in section of one example of the prior art objective optical system.
Figure 38:
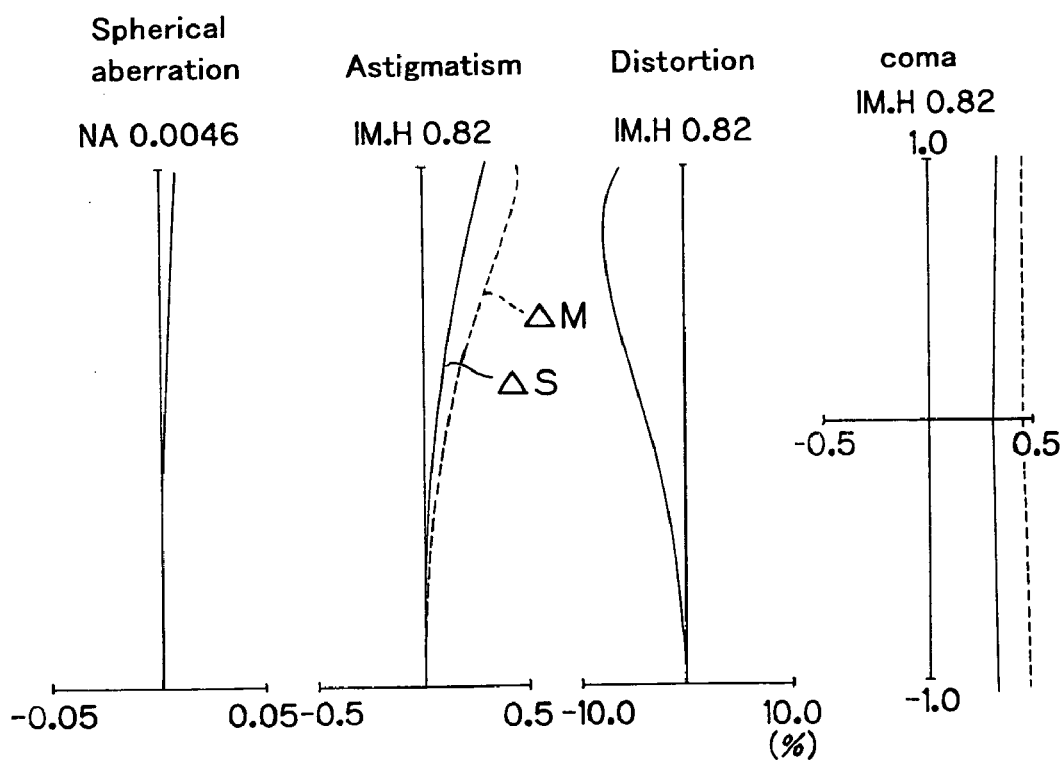
FIG. 38 is an aberration diagram for another example of the prior art objective optical system.

Regarding a prior art optical system (FIG. 37), a chief ray for the maximum image height is illustrated in FIG. 1(b) in terms of a thin lens system. Intersecting an optical axis at an aperture stop AS, the chief ray is refracted through a convex lens (the second lens) L2 located just after the stop AS, followed by repeated refractions to form an image. A relatively long distance between the aperture stop AS and the convex lens L2 after it causes the ray to grow high. As a result, refraction (occurring in the circle in FIG. 1(b)) at the convex lens L2 just after the stop is bent in a direction drawing near to the optical axis, producing negative distortion.

In the invention, therefore, a stop AS is located just before the second lens (convex lens) L2, as depicted in FIG. 1(a). In turn, this causes the refraction of an off-axis chief ray at the curved surface of the second lens L2 to be bent in a direction away from the optical axis, as occurring in the circle in FIG. 1(a); that is, the second lens L2, albeit being a convex lens, can produce positive distortion. In other words, while a rear unit (the third lens L3 and the fourth lens L4) is kept in a convex arrangement, there can be an effect of the concave lens L1 in a front unit on correction of negative distortion.

Condition (1) is generally about the ability to correct distortion and lens processability, and particularly about the aperture stop in the optical system, and the refractive index and focal length of the second lens L2 (the positive lens in the second group). If the stop is positioned on an image plane side with respect to the center of curvature of the curved surface of the second lens L2, then the chief ray is refracted at the curved surface of the second lens L2 in a direction away form the optical axis. As the lower limit of 2 to condition (1) is not reached, it renders it impossible to produce positive distortion, and has no effect on correction, because off-axis rays do not flip up at the convex surface of the second lens L2 in a direction away from the optical axis. Exceeding the upper limit of 6 is not preferable for lens processing, because it causes the second lens L2 to become way too thin.

Condition (2) is generally about the angle of field, and particularly about the focal length of the whole optical system and the focal length of the first lens L1 (negative meniscus lens) in the first group. Exceeding the upper limit of −0.9 to condition (2) allows the optical system to have a wide-angle arrangement, yet it is not preferable because there is an increased distortion. Falling below the lower limit of −2.3 is not again preferable, because an angle of field of greater than 70° fit for an endoscope is not obtainable.

Further in the invention, the rear unit is divided into the third group and the fourth group, wherein the third group is provided with a relatively tight concave surface having an air-contact surface, and the fourth group is made up of a cemented lens consisting of a positive lens and a meniscus lens and having a positive refracting power as a whole, with no air-contact concave surface provided to it. By doing so, it is possible to achieve an optical system with distortion corrected and no too much field curvature, as embodied by condition (3). As the Petzval's sum due to the concave surface in the third group does not reach the lower limit of −0.6 to condition (3), there are field curvature and distortion remaining undercorrected. Exceeding the upper limit of −0.2 causes too much field curvature to make the image plane flat. Prior art endoscopic optical systems with less distortion are set forth in Examples 1 and 2 of Patent Publication 4 referred to above. However, they are PS3=−0.09 and PS3=−0.04 departing from condition (3) (see Table 1).

Condition (4) is about the cementing vitreous material for the fourth group. The fourth group that gains the highest ray height ever in the rear unit has an enhanced effect on correction of chromatic aberrations at a cementing surface. Falling below the lower limit of 50, and exceeding the upper limit of 30, to condition (4) is not preferable because there is much chromatic aberration of magnification produced.

Condition (5) is about the power profile of the fourth group, and provided to control the angle of incidence of light rays on the image pickup plane. Falling below the lower limit of 2.3 to this causes the refracting power of the fourth group to grow large, so that an exit pupil cannot be more separated from the image pickup plane, failing to make the angle of incidence of light rays small.

Figure 2:
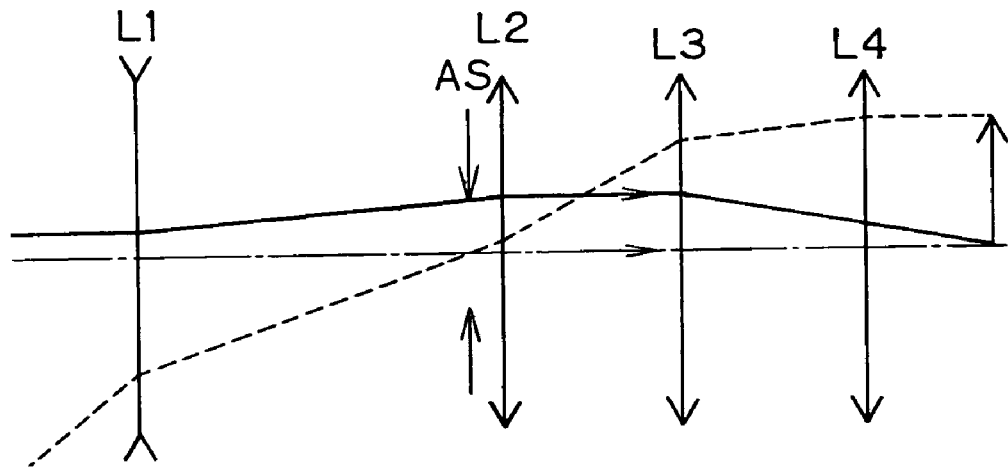
FIG. 2 is illustrative of the refraction of an axial marginal ray through the inventive endoscopic objective optical system.

Next, the invention is explained with reference of a specific rotation optical system that makes its image pickup plane rotatable. To correct an image by rotation, there is no choice but to have a structure wherein the optical system is mechanically separated into a front unit and a rear unit. As a result, there is an engagement between the front unit and the rear unit and, of course, some clearance is needed, giving rise to relative decentration of the front unit and the rear unit. In the invention, the front unit (the first lens L1 and the second lens L2) and the rear unit (the third lens L3 and the fourth lens L4) are designed to have a substantially afocal relation to each other, as can be seen from FIG. 2. This allows the exit pupil of the rear unit to be positioned nearly at infinity, and even with a vertical displacement of the front unit to the longitudinal direction of the endoscope, there is no paraxial displacement of an image-formation position. Further, even with relative rotation of the front unit and the rear unit, any displacement of the center of the field can be minimized.

Figure 3:
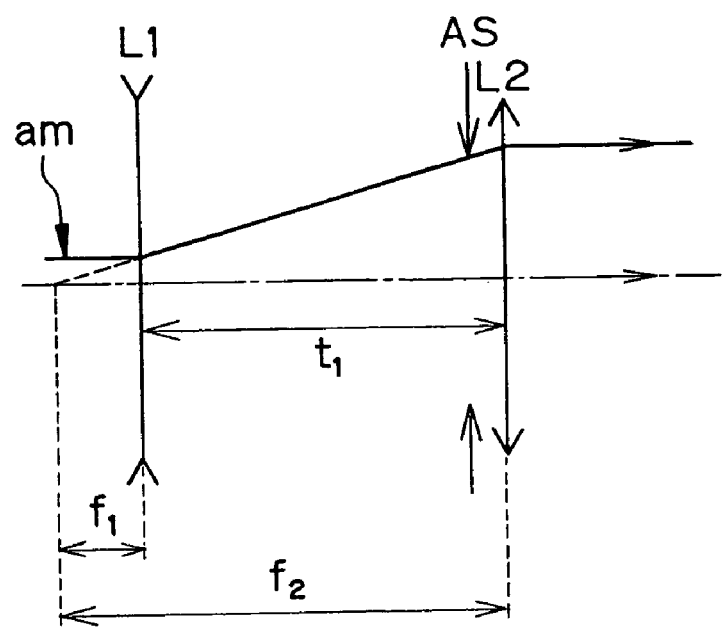
FIG. 3 is illustrative of the focal lengths of, and the space between, the first unit and the second unit in the inventive endoscopic optical system.

An object plane is larger enough than the focal length of the whole optical system and, as depicted in FIG. 3, an axial marginal ray coming from the object plane is incident as parallel light on it. That ray is flipped up by the concave action of the first lens L1, narrowed down through the aperture stop AS, and refracted by the convex action of the second lens L2 in the optical axis direction. To collimate the marginal light ray parallel with the optical axis (the axis of rotation), the rear focal position of the first lens L1 should be in alignment with the front focal position of the second lens L2. Here the relations of the focal lengths $f_1$ and $f_2$ of the first lens L1 and the second lens L2 to their spacing $t_1$ are represented by $$t_1 = f_2 - |f_1|$$

As long as this relation is satisfied, there can be a substantially axial afocal arrangement achieved between the front unit and the rear unit. In a hands-on oblique-vision optical system application, however, there need be a prism for changing the field direction, meaning that the value of $t_1$ is subject to a certain restriction. Condition (6) is indicative of the relation between the focal lengths $f_1$ and $f_2$ due to the optical path length taken by that prism and the outer diameter of the front lens. Exceeding the upper limit of 1.5 is not preferable, because the height of rays through the first lens L1 grows high, and the outer diameter of a cover glass at the front with no refracting power grows large, incurring an increase in the diameter of the endoscope. Further, falling below the lower limit of −0.3 is again not preferable, because the optical path length for two reflections within the prism becomes insufficient, and there is no choice but to change the field direction by a single one reflection, resulting in an inverted or mirror image.

It is here noted that the arrangement of the invention wherein the angle of incidence of axial marginal rays from the front unit on the rear unit is substantially parallel with the axis of rotation implies an allowance of ±3°.

Examples 1 to 15 of the endoscopic objective optical system according to the invention are now explained.

EXAMPLE 1

Figure 4:
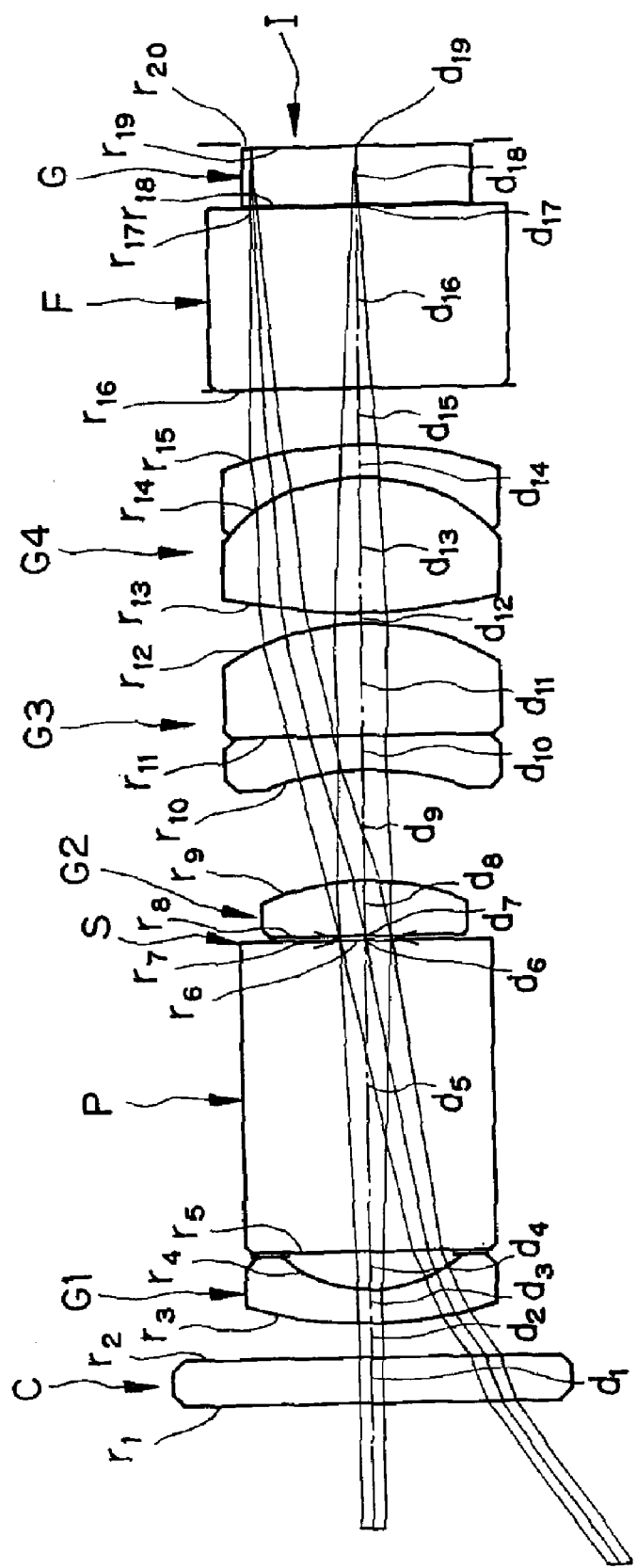
FIG. 4 is an optical path representation for the endoscopic objective optical system according to Example 1 of the invention.
Figure 22:
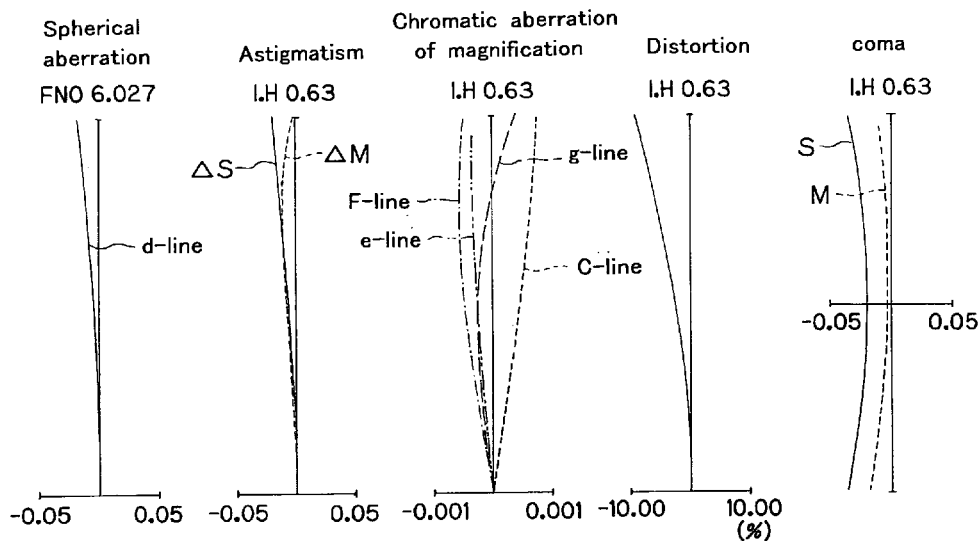
FIG. 22 is an aberration diagram illustrative of the spherical aberration, astigmatism, chromatic aberration of magnification, distortion and coma of the endoscopic objective optical system according to Example 1.
Figure 23:
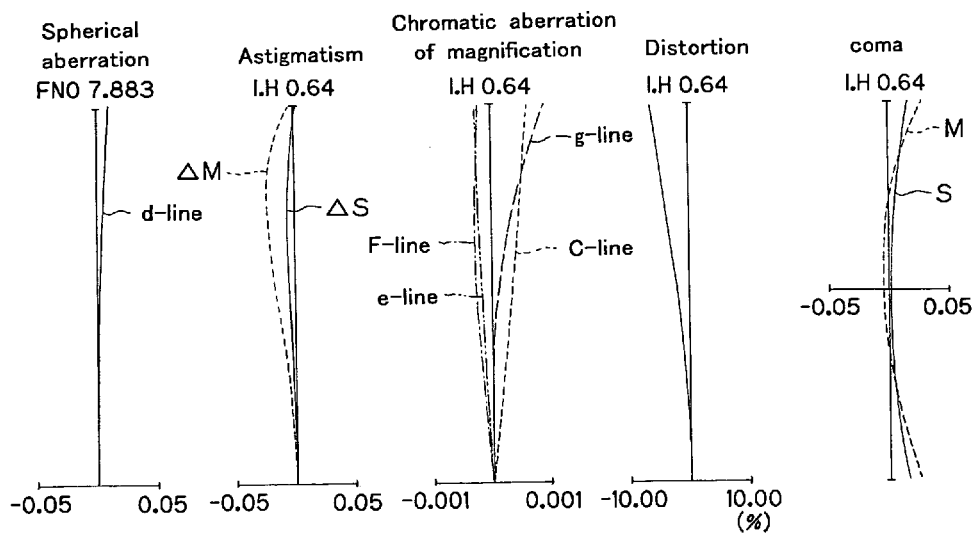
FIG. 23 is an aberration diagram, as in FIG. 22, for the endoscopic objective optical system according to Example 2.

FIG. 4 is a representation of the optical path taken by the endoscopic objective optical system according to the invention, and FIG. 22 is an aberration diagram indicative of the spherical aberration, astigmatism, chromatic aberration of magnification, distortion and coma of the endoscopic objective optical system of Example 1. Throughout the present disclosure, "FNO" and "I.H" are indicative of an F-number and an image height, respectively. The endoscopic objective optical system here is built up of, in order from its object side, a cover glass C for the objective optical system, a first group G1 composed of a negative meniscus lens convex on its object side, a plane-parallel plate P, a stop S, a second group G2 composed of a positive lens with a plane on its object side, a third group G3 composed of a cemented lens consisting of a concavo-plano negative lens and a plano-convex positive lens, and a fourth group G4 composed of a cemented lens consisting of a double-convex positive lens and a negative meniscus lens convex on its image plane side. Via an infrared cut filter F and a CCD cover glass G, an object image is formed on an image pickup plane I.

As can be seen from FIG. 4, a chief ray at the convex surface of the convex lens (the second group G2) just after the stop S is refracted in a direction away from the optical axis. Further, the cementing surface in the fourth group G4 has a negative refracting power, and at that surface having a high ray height, too, the chief ray is refracted in a direction away from the optical axis for correction of distortion. The angle of incidence on the image pickup plane I of the CCD is about 3° at the maximum image height.

The concave surface in the third group G3 works for correction of field curvature, and the whole refracting power of the fourth group G4 is weak, working primarily for correction of coma, astigmatism and chromatic aberration of magnification.

The plano-convex lens (the second lens, the second group G2) located just after the stop S refracts the chief ray just after the stop S; with a tilt to it, there is an asymmetric refraction of chief rays above and below the optical axis, which may otherwise cause local blurs on the image pickup plane.

To prevent such a tilt and overcome such a blurring problem, the plane side is designed to provide an abutment against the plane-parallel plate P on the object side, as herein. In addition, the plane-parallel plate P interposed between the first lens (the first group G1) and the second lens (the second group G2) behaves as an optical path taken by a prism in the case where the optical system here is set up as an oblique-vision optical system. If this is dispensed with, astigmatism and chromatic aberrations will become worse. When a direct-vision optical system and an oblique-vision optical system are built up of the same lenses, it is preferable for the direct-vision optical system to place in it a plane-parallel plate P having a length corresponding to the prism's optical path length.

Lens data on this example will be given later. The same will apply to the following examples.

EXAMPLE 2

Figure 5:
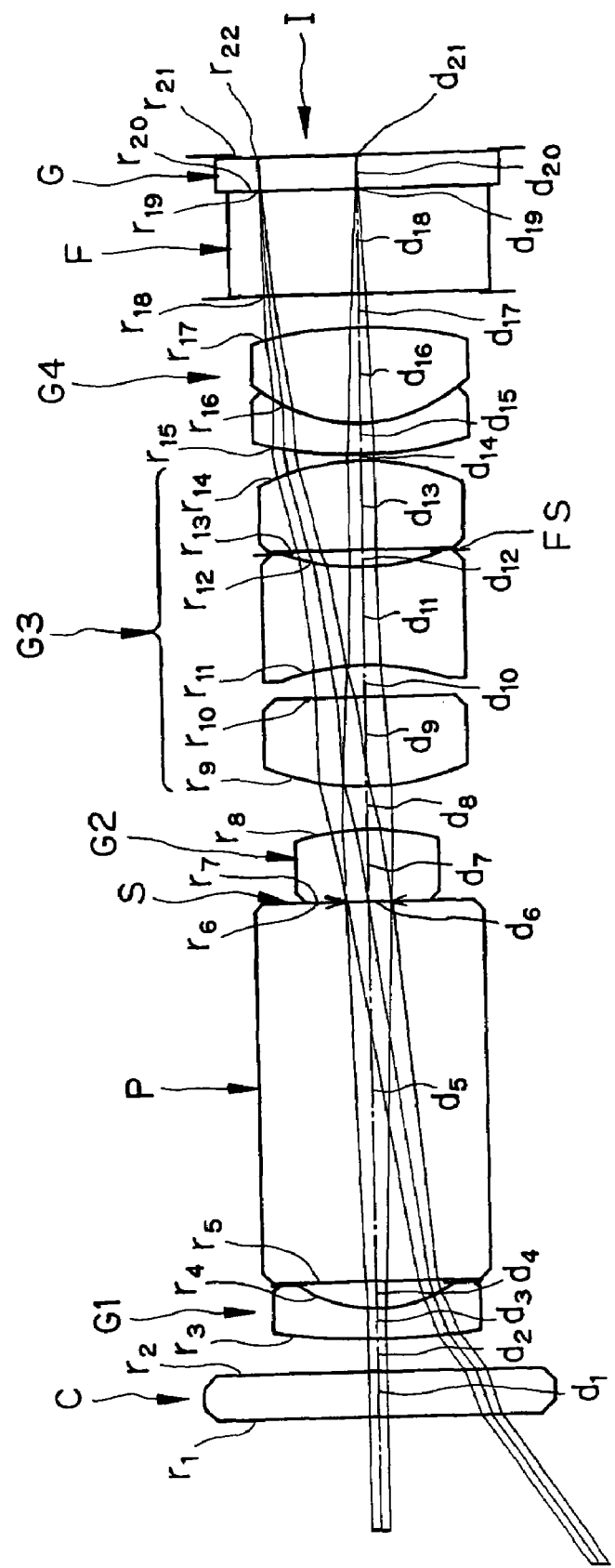
FIG. 5 is an optical path representation for the endoscopic objective optical system according to Example 2 of the invention.

FIG. 5 is an optical path diagram for the endoscopic objective optical system of Example 2 according to the invention, and FIG. 22 is an aberration diagram, as in FIG. 22, for the endoscopic objective optical system of Example 2. Example 2 is the same as Example 1 with the exception that the third group G3 is made up of a convex-plano positive lens convex on its object side, a double-concave negative lens and a plano-convex positive lens convex on its image plane side, and the fourth group G4 is composed of a cemented lens consisting of a negative meniscus lens convex on its object plane side and a double-convex positive lens. Via an infrared cut filter F and a CCD cover glass G, an object image is formed on an image pickup plane I.

A chief ray at the convex surface of the second lens (the second group G2) just after the stop S is refracted in a direction away from the optical axis, producing positive distortion. Further, this corrects distortion at the image-side surface in particular of the negative lens in the third group G3 into positive one with the result that distortion is as small as about −6.4% at the maximum image height. The negative action of the cementing surface in the fourth group G4 makes correction of distortion and chromatic aberration of magnification. In the third group G3, the two plano-convex positive lenses are of the same kind that contributes favorably to cost reductions, and the double-concave negative lens has an equal curvature at both surfaces, convenient because of no need of telling which surface lies in which direction during assembling. In addition, there is a flare stop FS interposed between the double-concave negative lens and the image-plane-side plano-convex positive lens in the third group G3 for removal of ghost light ensuing from reflection from the CCD image pickup plane. Furthermore, a planar portion is provided to the concave surface of the double-concave negative lens in the third group G3 at a position facing the plane-convex positive lens on the image plane side, thereby minimizing the occurrence of decentration due to a tilt within a mechanical frame.

EXAMPLE 3

Figure 6:
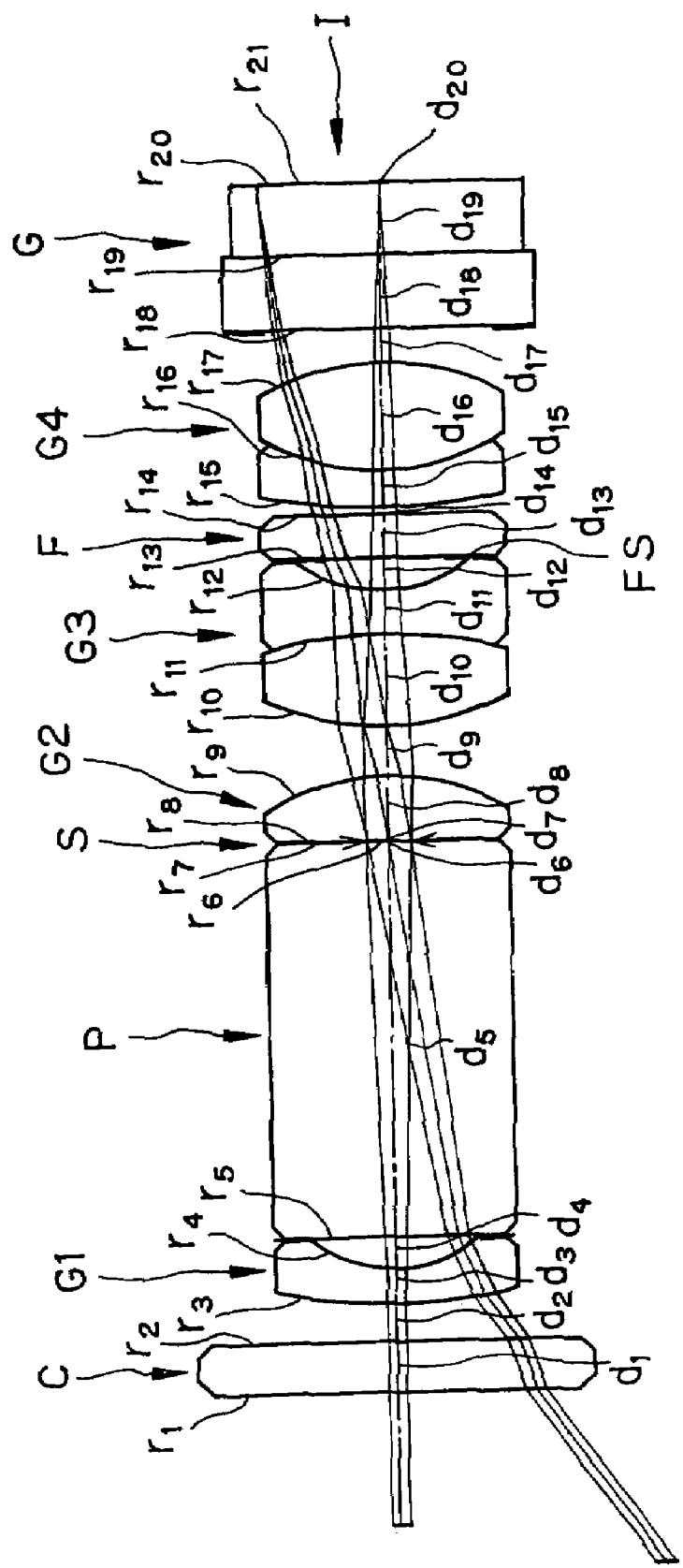
FIG. 6 is an optical path representation for the endoscopic objective optical system according to Example 3 of the invention.
Figure 24:
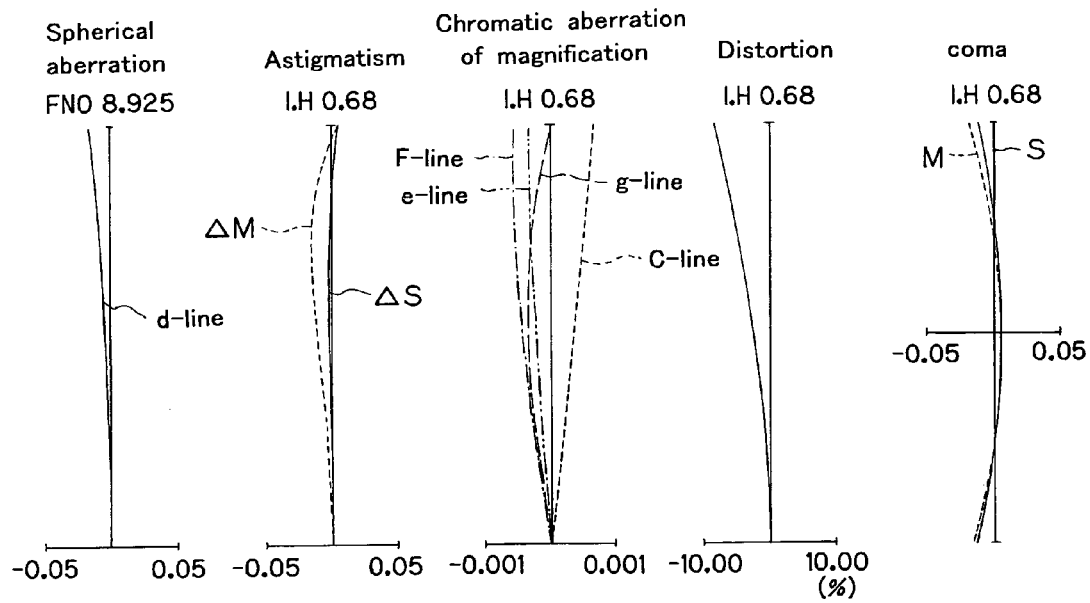
FIG. 24 is an aberration diagram, as in FIG. 22, for the endoscopic objective optical system according to Example 3.

FIG. 6 is an optical path diagram for the endoscopic objective optical system of Example 3 according to the invention, and FIG. 24 is an aberration diagram, as in FIG. 22, for the endoscopic objective optical system of Example 3. Example 3 is the same as Examples 1 and 2 with the exception that the third group G3 is composed of a cemented lens consisting of a double-convex positive lens and a double-concave negative lens and the fourth group G4 is composed of a cemented lens consisting of a negative meniscus lens convex on its object side and a double-convex positive lens, with an infrared absorption filter F interposed between them. Via a CCD cover glass G, an object image is formed on an image pickup plane I.

The action of the second lens is the same as in Examples 1 and 2, and distortion and chromatic aberration of magnification are corrected through the negative action of the air-contact surface in the third group G3. Distortion is −8.8% at the maximum image height. The third group G3 is bonded to a plane-parallel plate just after it, so that the edge thickness (the lens's periphery length) is increased to hold back decentration due to a tilt. Between the third group G3 and an absorption filter F, there is a stop FS interposed to prevent flares from reflections from the CCD image pickup plane. The infrared filter F could be applied with a YAG laser (of 1,076 nm in wavelength) cut coating, a semiconductor laser (of 805 nm in wavelength) cut coating or the like, in addition to an ordinary antireflection coating. In consideration of the characteristics of the interference filter, it is then preferable to set the angle of incidence at 25° or less, because there is a reduced cut wavelength shift, and laser cutting is possible as well.

In general, an imaging optical system has in it an infrared cut filter for cutting off unwanted light in the infrared region. That cut filter is broken down into an interference filter using a multilayer film and an absorption type filter designed to cut off infrared radiation by the material itself. Because the interference type filter has the demerits of being apt to producing flares or ghosts, with restrictions on the incident angle, the absorption type filter is often used. The infrared absorption filter has a larger thermal expansion coefficient than have general optical glasses, and with it applied or otherwise bonded to a CCD image pickup plane or the like, the bonding surface may often peel off upon sterilized at high temperatures or the like. To stay off such inconvenience, the absorption filter should preferably be placed in the optical system, as herein, rather than bonded to the CCD.

As already noted with reference to the prior art endoscope, a telecentric optical system is more suitable for the purpose of preventing a decrease in the quantity of light. With recently developed imaging devices, however, a microlens located just before the image pickup plane is so tweaked that the angle of incidence at which there is no decrease in the quantity of light can be tilted to the vertical, thereby meeting the demand for size reductions of the endmost portion of an endoscope. Some optical systems today are free from light quantity decreases even at an angle of incidence of up to about 20°. In the instant example, the angle of incidence of the chief ray on the image pickup plane is set at 11°.

EXAMPLE 4

Figure 7:
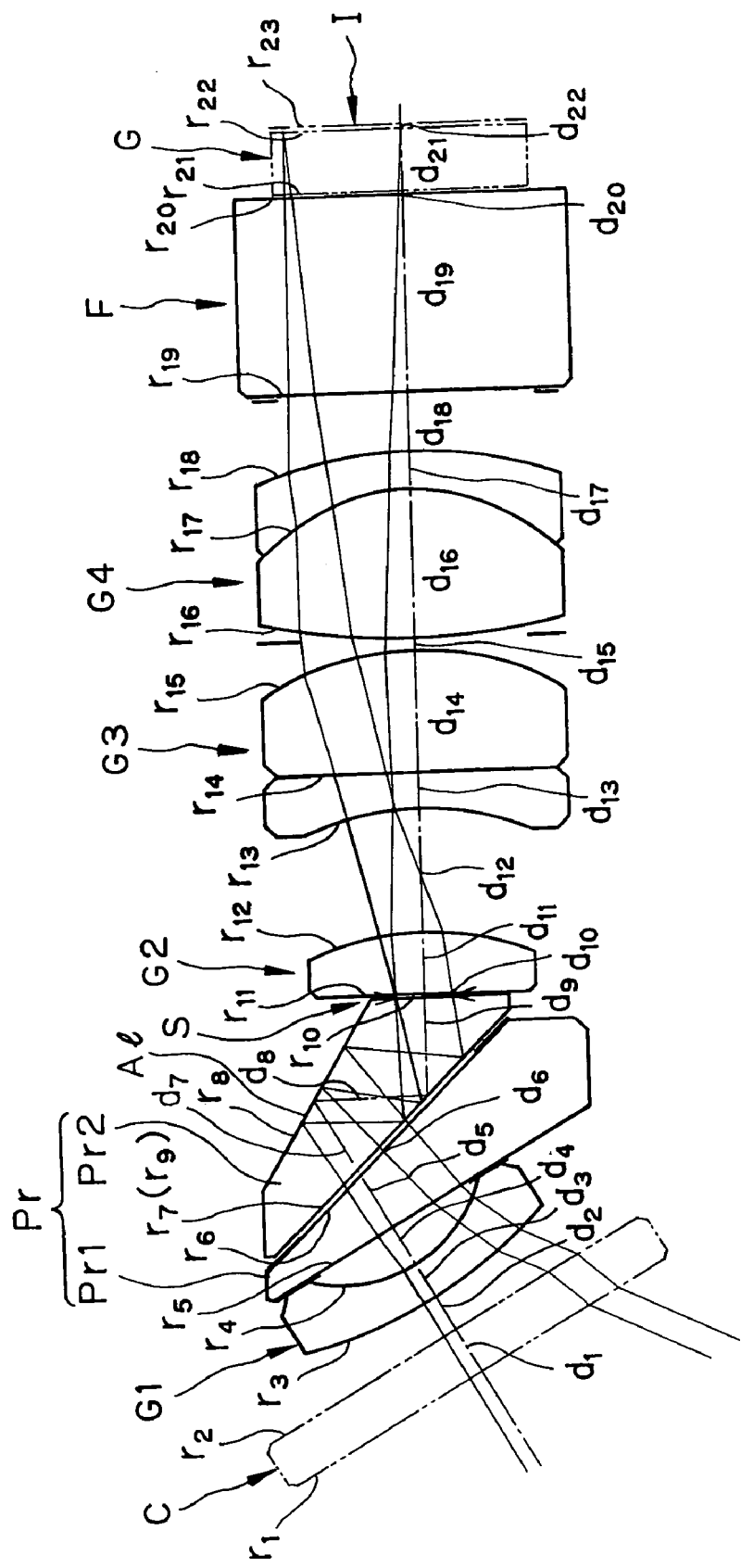
FIG. 7 is an optical path representation for the endoscopic objective optical system according to Example 4 of the invention.
Figure 25:
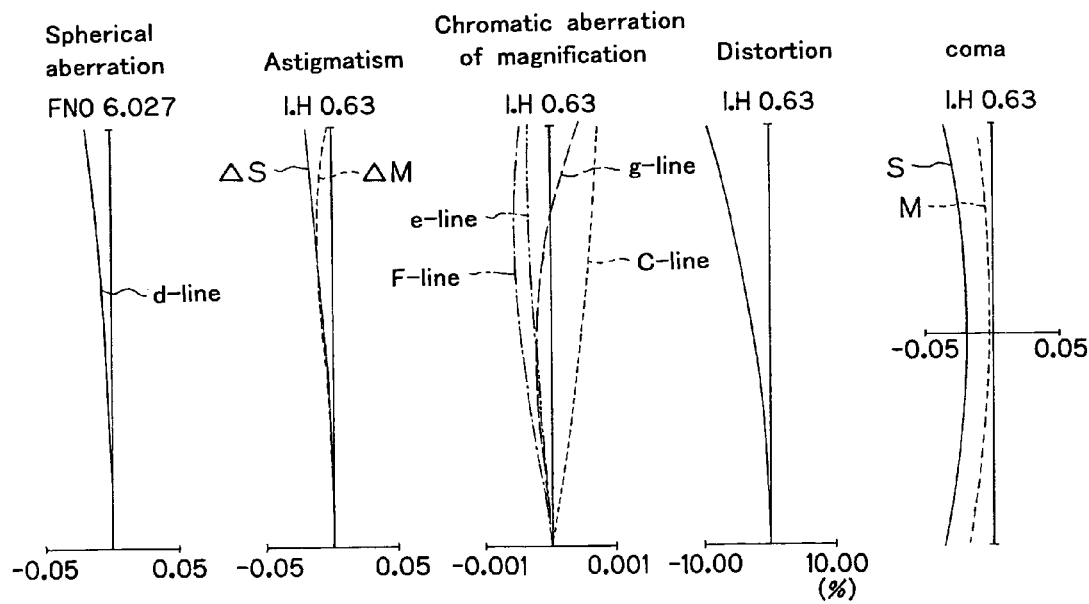
FIG. 25 is an aberration diagram, as in FIG. 22, for the endoscopic objective optical system according to Example 4.
Figure 30:
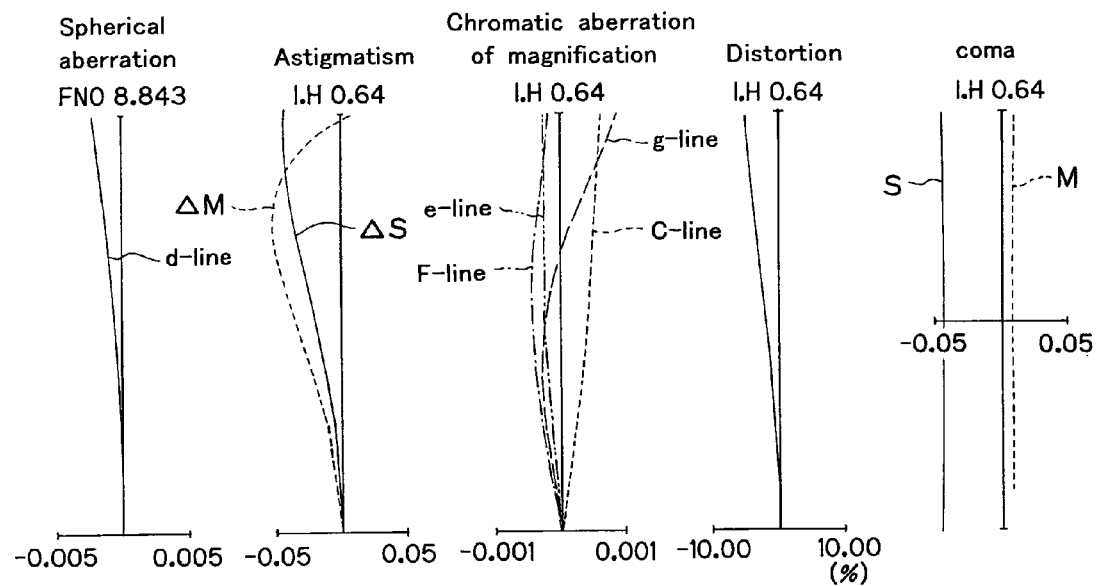
FIG. 30 is an aberration diagram, as in FIG. 22, for the endoscopic objective optical system according to Example 9.
Figure 31:
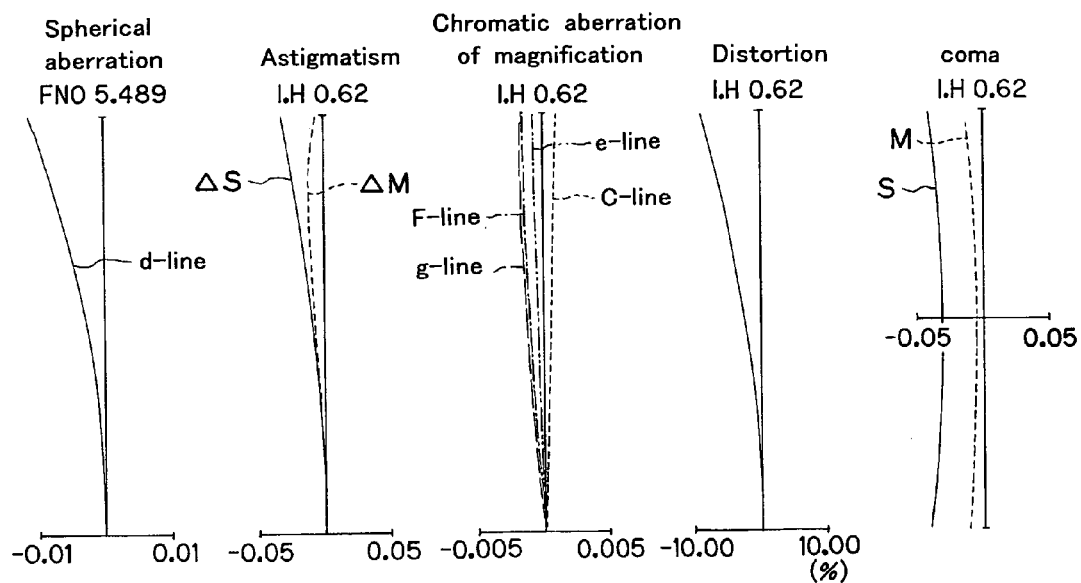
FIG. 31 is an aberration diagram, as in FIG. 22, for the endoscopic objective optical system according to Example 10.
Figure 32:
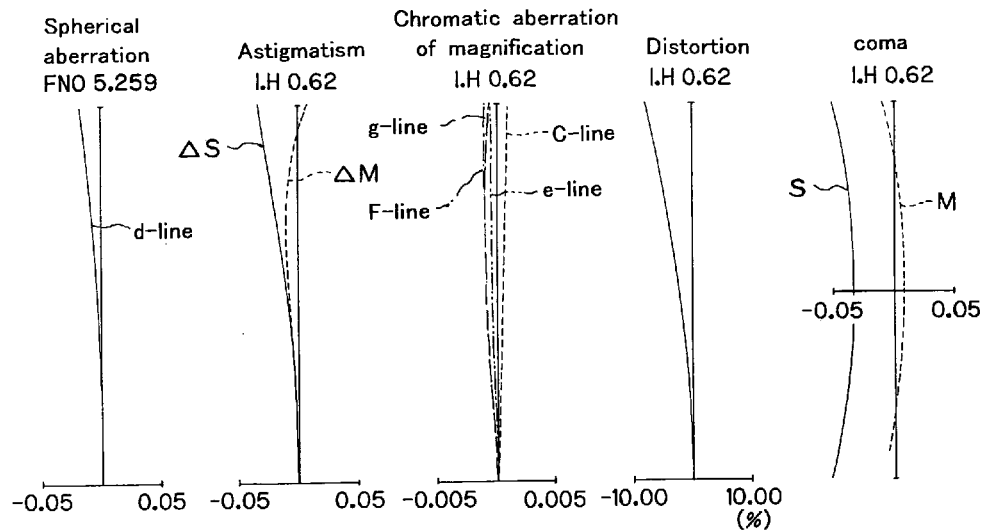
FIG. 32 is an aberration diagram, as in FIG. 22, for the endoscopic objective optical system according to Example 11.
Figure 33:
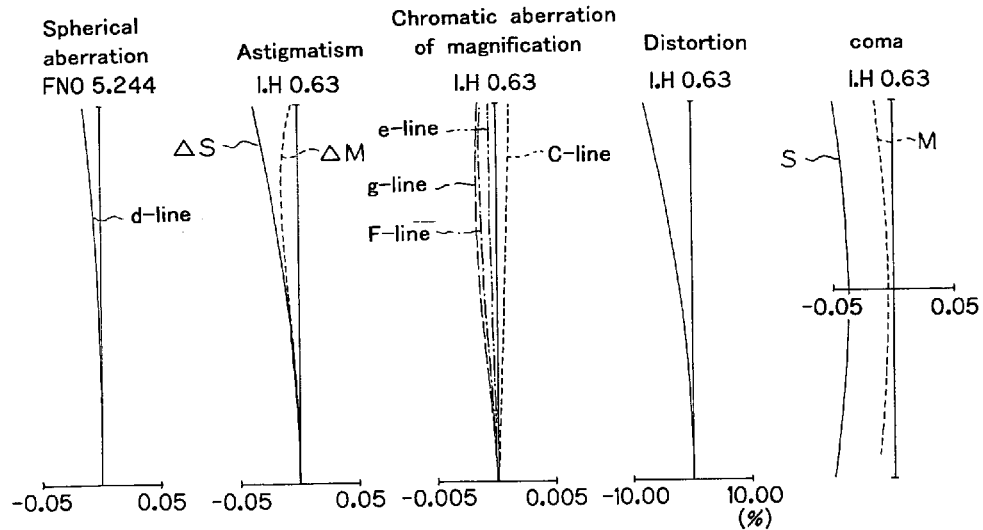
FIG. 33 is an aberration diagram, as in FIG. 22, for the endoscopic objective optical system according to Example 12.
Figure 34:
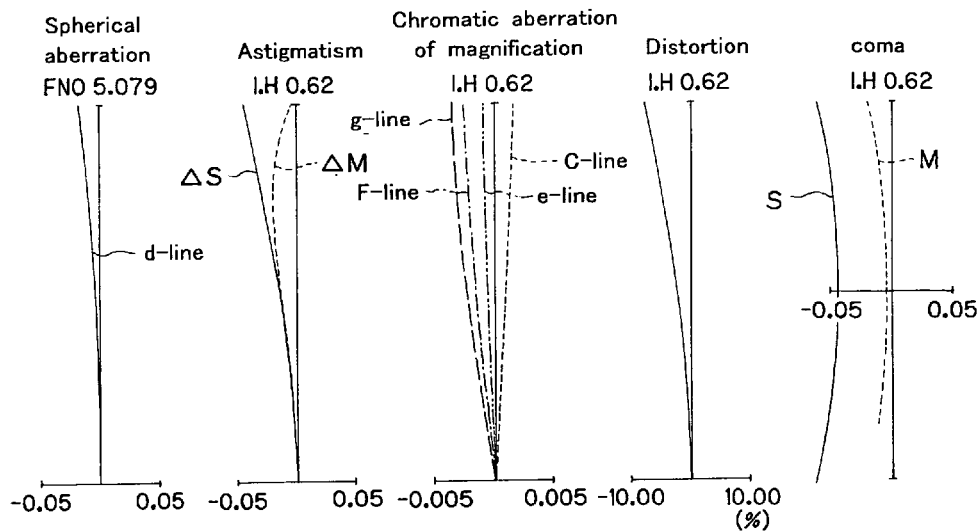
FIG. 34 is an aberration diagram, as in FIG. 22, for the endoscopic objective optical system according to Example 13.
Figure 35:
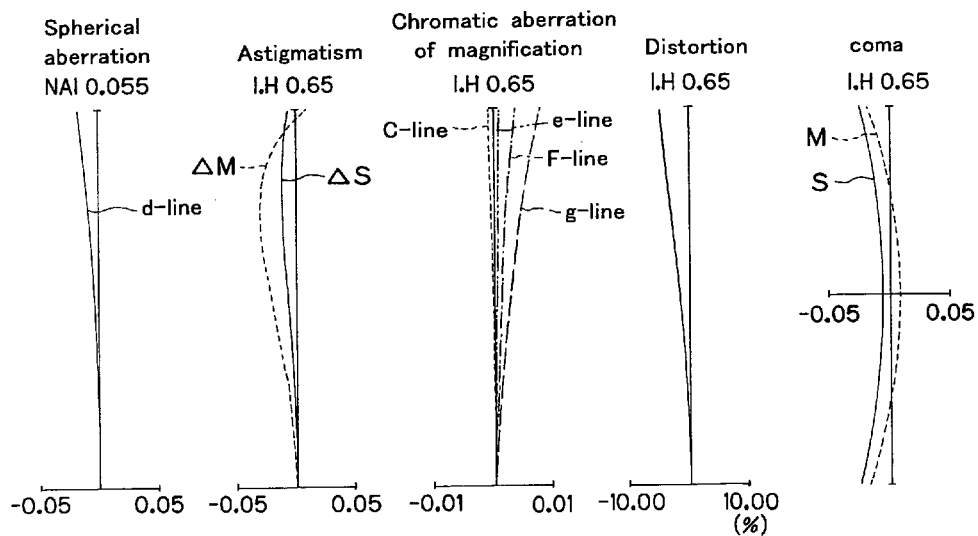
FIG. 35 is an aberration diagram, as in FIG. 22, for the endoscopic objective optical system according to Example 14.
Figure 36:
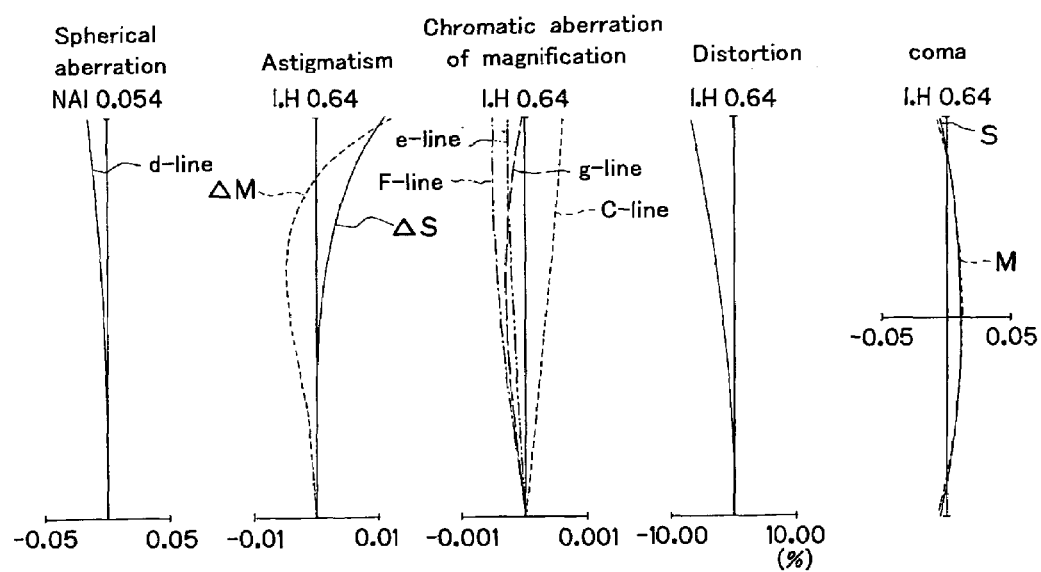
FIG. 36 is an aberration diagram, as in FIG. 22, for the endoscopic objective optical system according to Example 15.

FIG. 7 is an optical path diagram for the endoscopic objective optical system of Example 4 according to the invention, and FIG. 25 is an aberration diagram, as in FIG. 22, for the endoscopic objective optical system of Example 4. In this example, a prism set Pr is provided to the tip portion of the optical system in such a way as to achieve a front oblique vision of 30°. Passing through a cover glass C, the first lens that forms the first group G1, the first prism Pr1 and the second prism Pr2 in this order from the object side, light is reflected at an aluminum coating A1 on the bottom of the second prism Pr2, and then totally reflected at the side of the second prism Pr2 facing the first prism Pr1, going toward the side of the second lens that forms the second group G2. The rest of the optical system is the same as in Example 1.

This prism set Pr is preferably designed such that at the side of the second prism Pr2 facing the first prism Pr1, the light is separated into a transmitted light beam and a reflecting light beam; this ensures that there is no shading of light rays by the aluminum coating A1 and so a constant illuminance is obtained on the image plane I.

In the space between the first prism Pr1 and the second prism Pr2, there is an air layer capable of total reflection of light within the second prism Pr2.

For making the critical angle of this total reflection large, it is preferable to make the refractive index of the second prism Pr2 high; in this example, nd=1.883, and the critical angle is about 32°. The angle of axial marginal rays between the second group G2 and the third group G3 is about −2.20 with respect to the optical axis, so that the movement of the center of an image on the image plane I is reduced with respect to the front unit (the first and the second group G2) and the rear unit (the third and the following group(s)).

The spacing between the front unit and the rear unit should preferably be wide to some degrees so as to lend itself to a mechanical engagement and variations of the movable part with rotation. Too narrow a spacing is not preferable, because the lenses often hit one upon another during assembling, which may do damages to their surfaces. Although the focal length of the endoscopic objective optical system according to this example is standardized, yet the spacing between the front unit and the rear unit is set at 1 mm during practical assembling.

EXAMPLE 5

Figure 8:
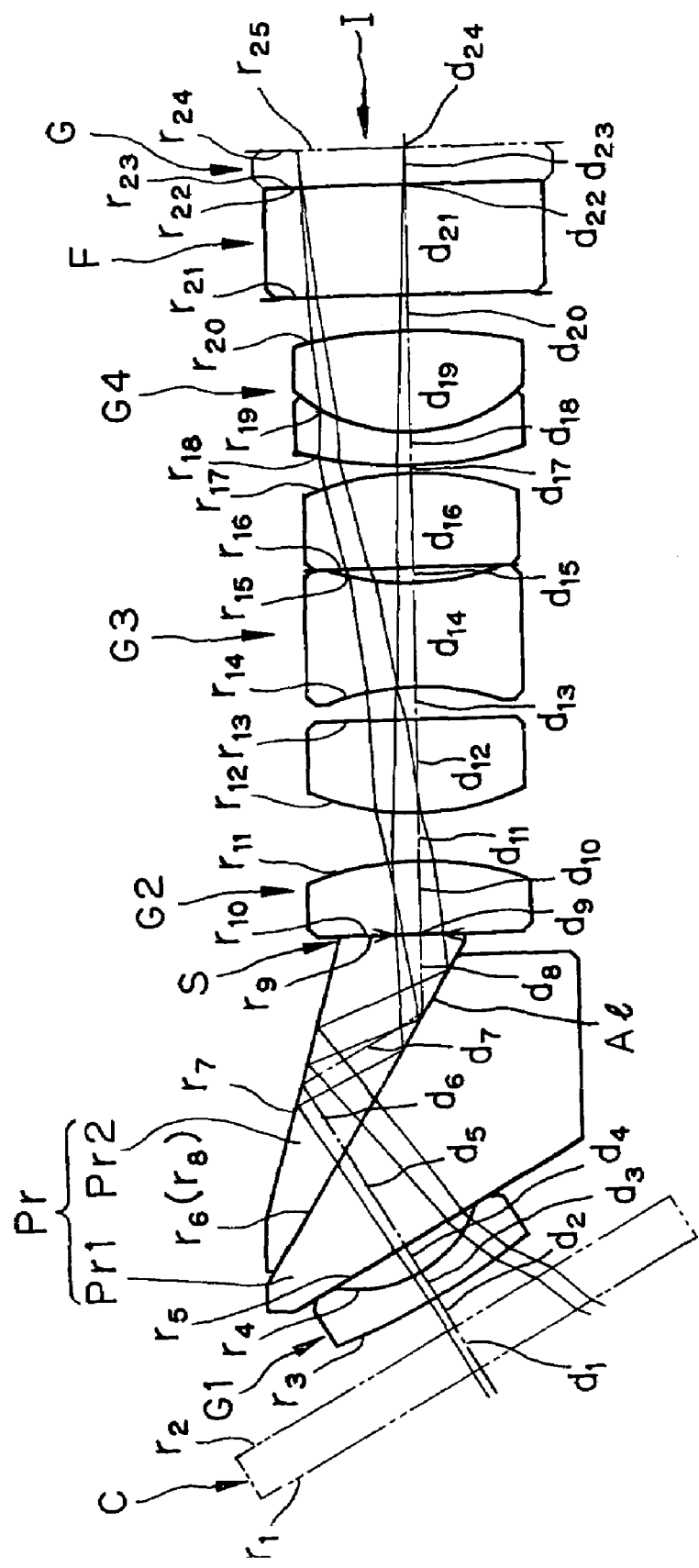
FIG. 8 is an optical path representation for the endoscopic objective optical system according to Example 5 of the invention.

FIG. 8 is an optical path diagram for the endoscopic objective optical system of Example 5 according to the invention, and FIG. 26 is an aberration diagram, as in FIG. 22, for the endoscopic objective optical system of Example 5. In this example, light passes through the first prism Pr1 and the second prism Pr2 by way of the same path as in Example 1; however, the light is totally reflected at the bottom of the second prism Pr2, and then reflected at an aluminum coating A1 applied on the side of the second prism Pr2 facing the first prism Pr1, entering the second lens that forms the second group G2. This type prism set is preferable, because, unlike Example 4, there is no need of having an air layer between the first prism Pr1 and the second prism Pr2; there are no vertically asymmetric aberrations (especially astigmatism) due to the wedge effect of the air layer. To make the critical angle of total reflection large, it is preferable for the prism vitreous material to have a higher refractive index: nd=1.883 with a critical angle of about 32°. The rest of the arrangement of this example is the same as in Example 2. The angle of axial marginal rays between the second group G2 and the third group G3 is about −0.7° with respect to the optical axis, which means that there is an afocal arrangement obtained. Thus, it is possible to minimize the movement of the image plane with respect to decentration of the front unit (the first and the second group G2) and the rear unit (the third G3 and the following group(s)).

FIGS. 9(a) and 9(b) are illustrative of an optical system of this example configured such that the front unit FG is engaged with the rear unit RG to rotate the rear unit G and a CCD unit IU in unison, and an optical system configured such that a CCD unit IU is rotated as set forth in Patent Publication 5, respectively, showing how axial light rays behave when the movable part is shifted +0.1 mm in a direction vertical to the optical path (↑). FIG. 9(b) is illustrative of a structure involving the movement of the CCD unit IU alone, as set forth in Patent Publication 5, wherein the center of the optical axis moves down by 0.1 mm—that is the same amount of shift of the CCD unit IU—with respect to the image pickup plane of the CCD. In the instant example depicted in FIG. 9(a), when the rear unit RG and the CCD unit IU are moved in the same manner, the movement of the optical axis with respect to the image pickup plane of the CCD is only 0.02 mm. It follows that with the arrangement wherein there is an afocal divide between the front unit FG and the rear unit RG in the optical system and the rear unit RG including the CCD unit IU is rotated, it is possible to obtain effects on minimizing image decentration.

EXAMPLE 6

Figure 10:
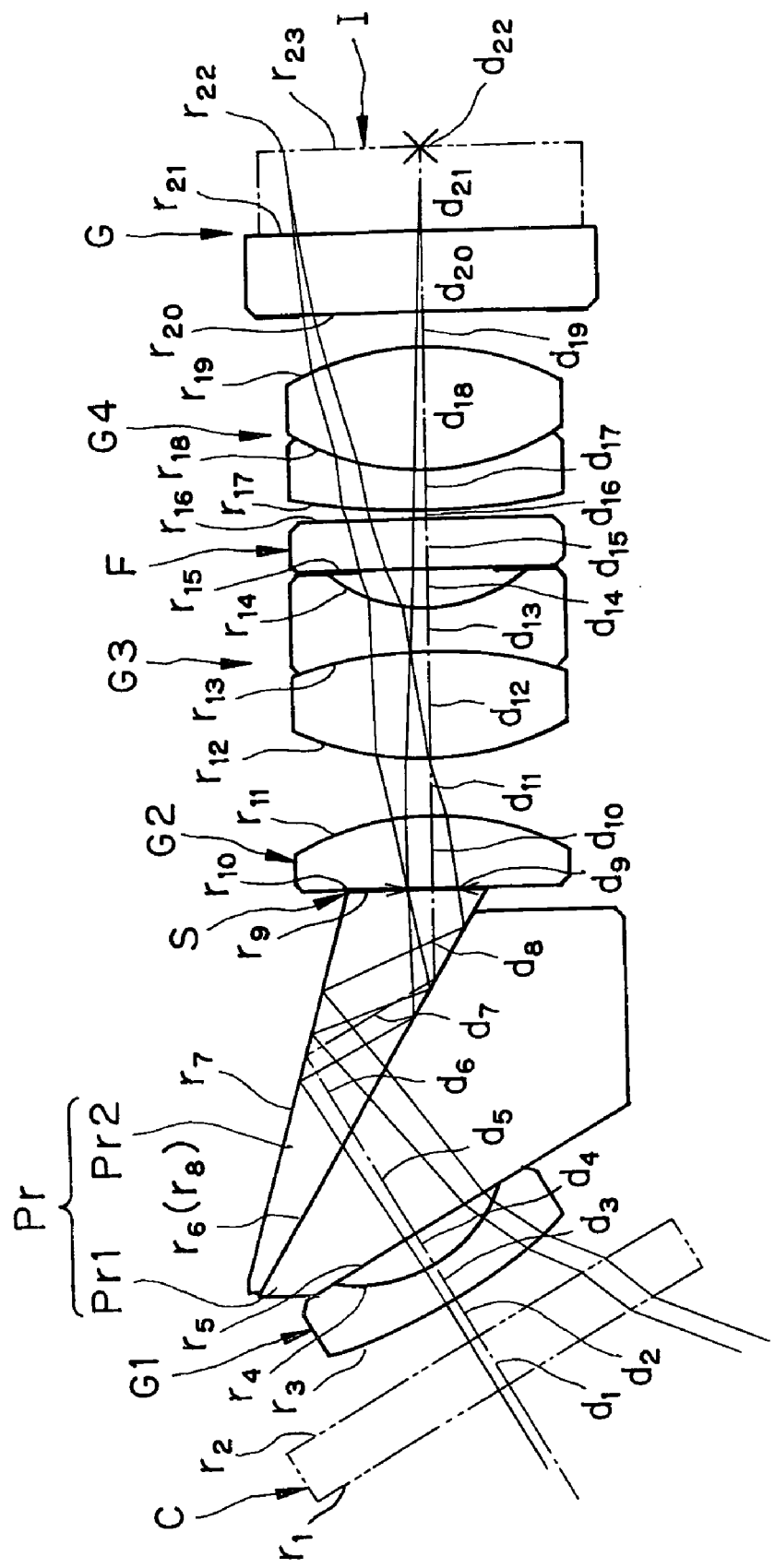
FIG. 10 is an optical path representation for the endoscopic objective optical system according to Example 6 of the invention.

FIG. 10 is an optical path diagram for the endoscopic objective optical system of Example 6 according to the invention, and FIG. 27 is an aberration diagram, as in FIG. 22, for the endoscopic objective optical system of Example 6. In this example, light passes through the first prism Pr1 and the second prism Pr2 by way of the same path as in Example 5, and the prism vitreous material is again the same as in Example 5. The rest of the arrangement is the same, too. The angle of axial marginal rays between the second group G2 and the third group G3 is about −1.8° with respect to the optical axis, which means that there is an afocal arrangement obtained. Thus, it is possible to minimize the movement of the center of an image on the image plane with respect to decentration of the front unit and the rear unit.

Figure 11:
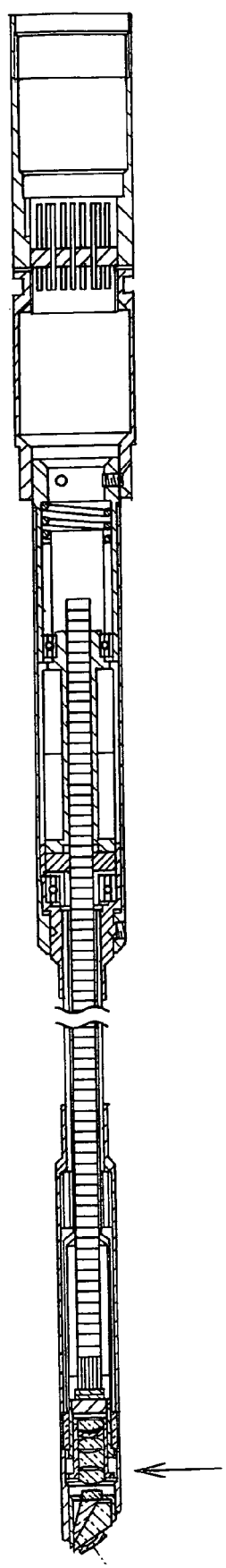
FIG. 11 is a sectional illustration of the internal structure of the insert of a hard endoscope, which is illustrative of what relation each of the optical systems of Examples 4-6 has to a mechanical frame.
Figure 12:
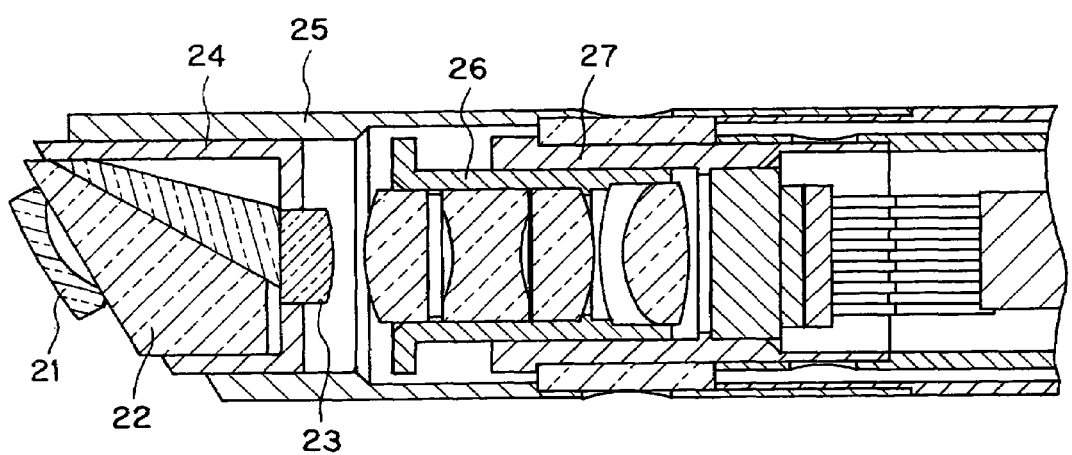
FIG. 12 is an enlarged view of the endmost portion of the insert of the hard endoscope depicted in FIG. 11.
Figure 13:
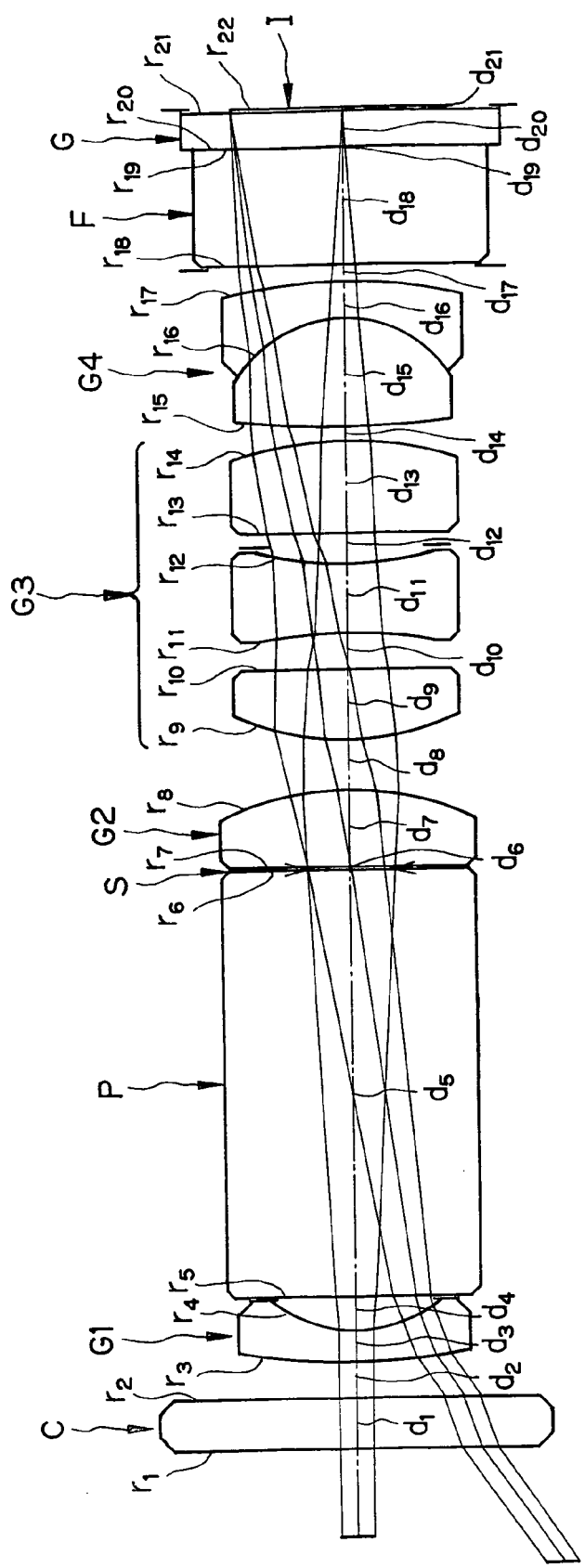
FIG. 13 is an optical path representation for the endoscopic objective optical system according to Example 7 of the invention.
Figure 14:
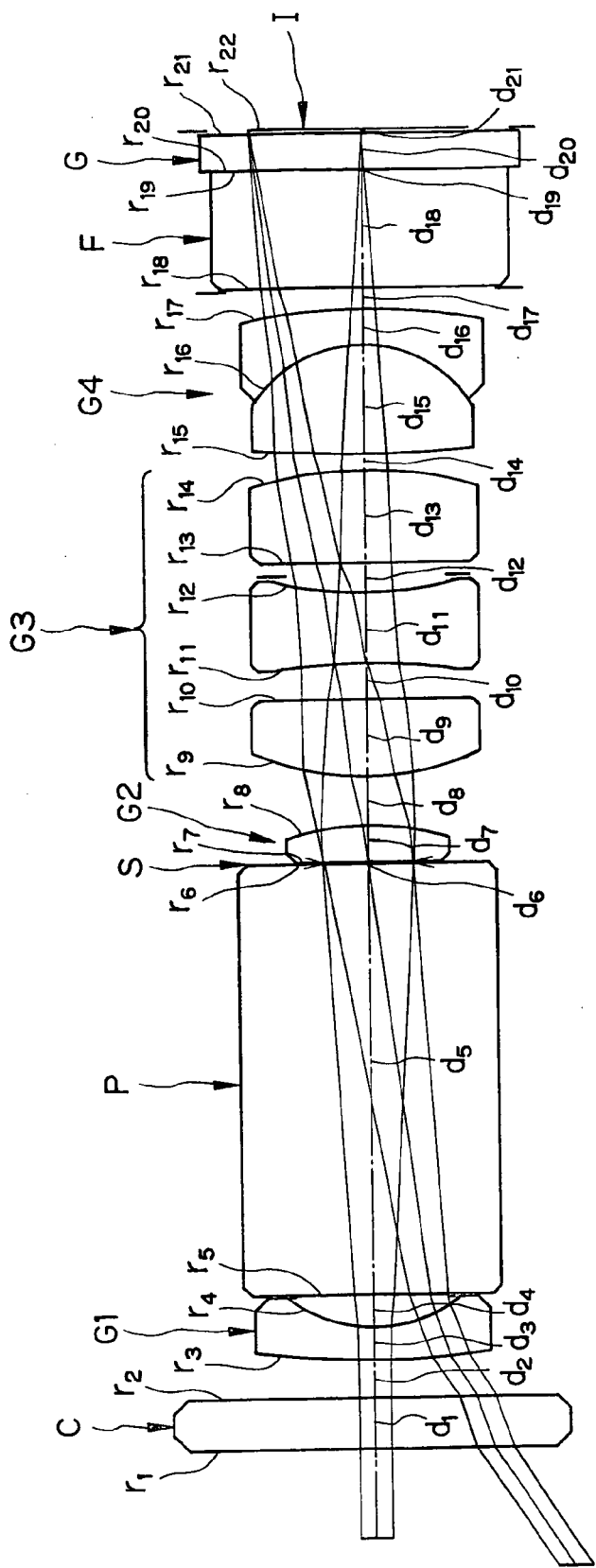
FIG. 14 is an optical path representation for the endoscopic objective optical system according to Example 8 of the invention.
Figure 15:
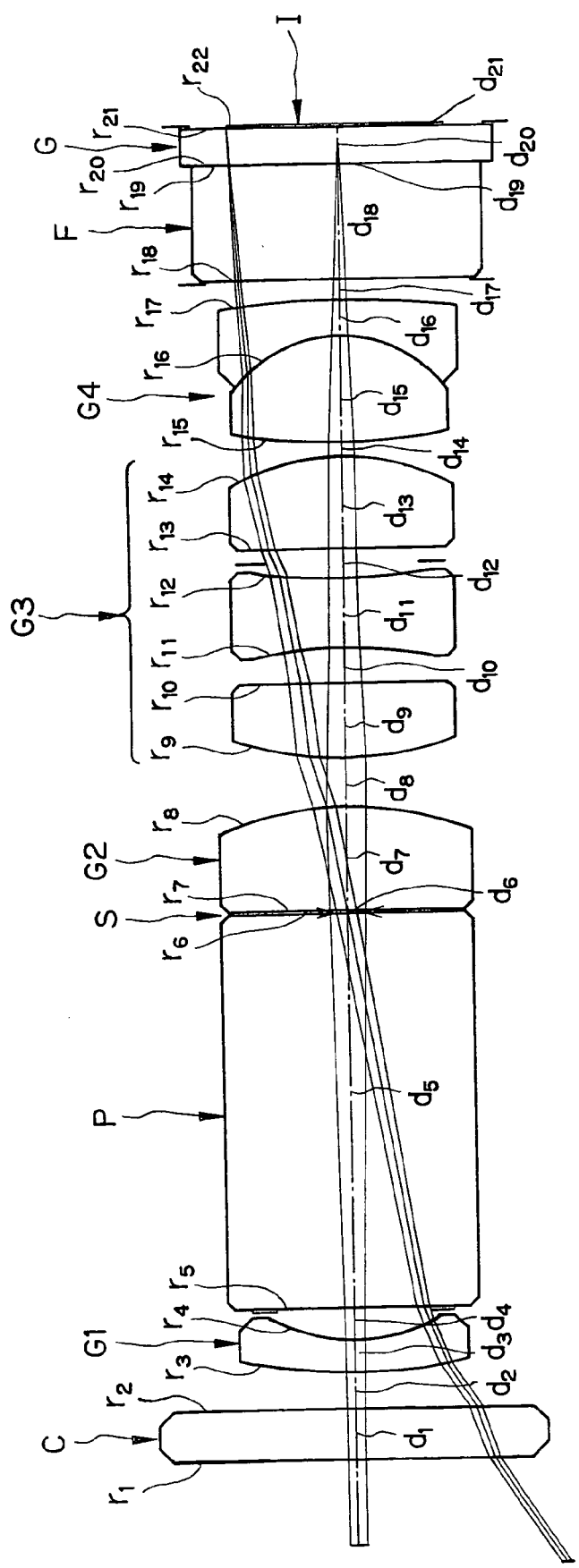
FIG. 15 is an optical path representation for the endoscopic objective optical system according to Example 9 of the invention.
Figure 16:
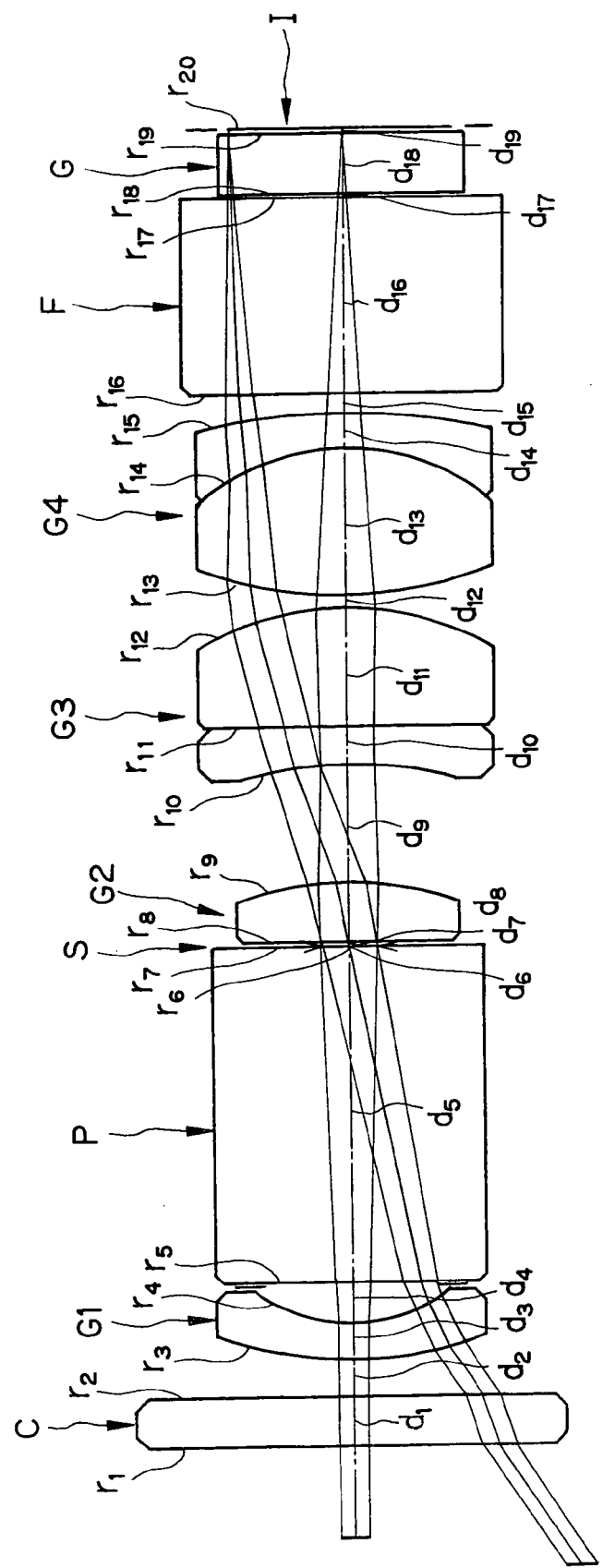
FIG. 16 is an optical path representation for the endoscopic objective optical system according to Example 10 of the invention.
Figure 17:
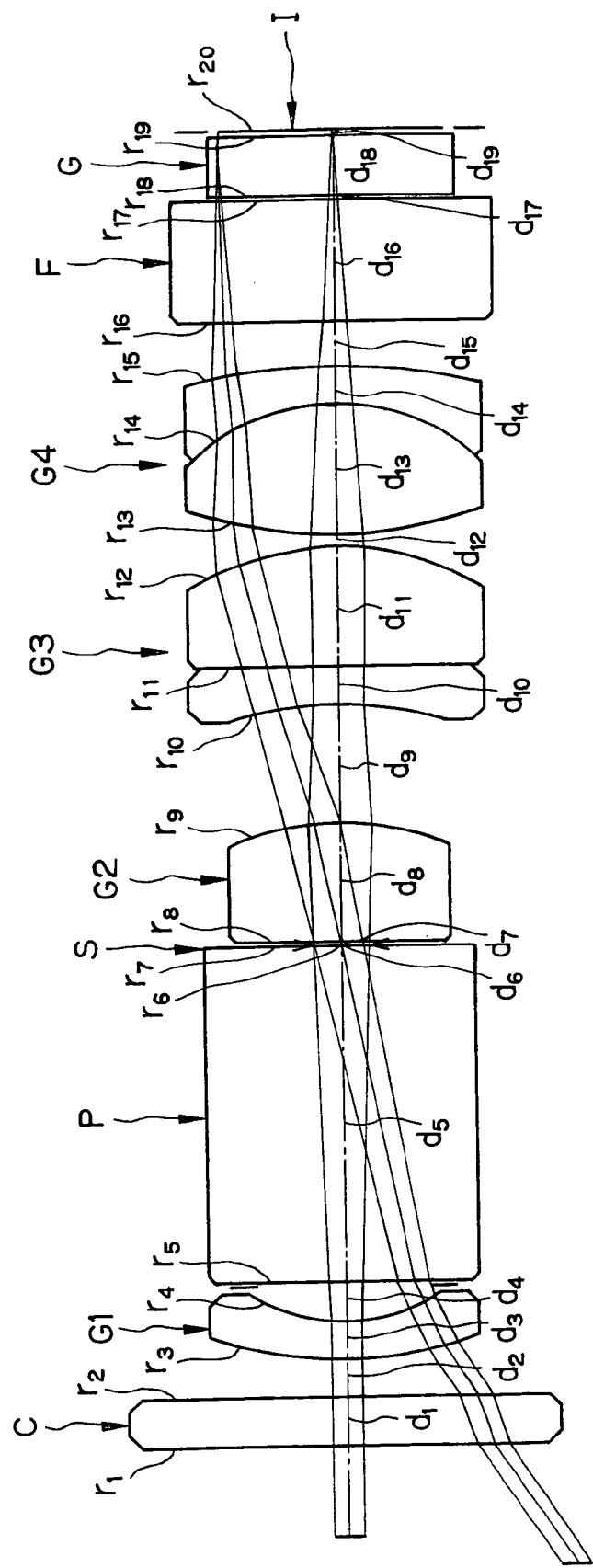
FIG. 17 is an optical path representation for the endoscopic objective optical system according to Example 11 of the invention.
Figure 18:
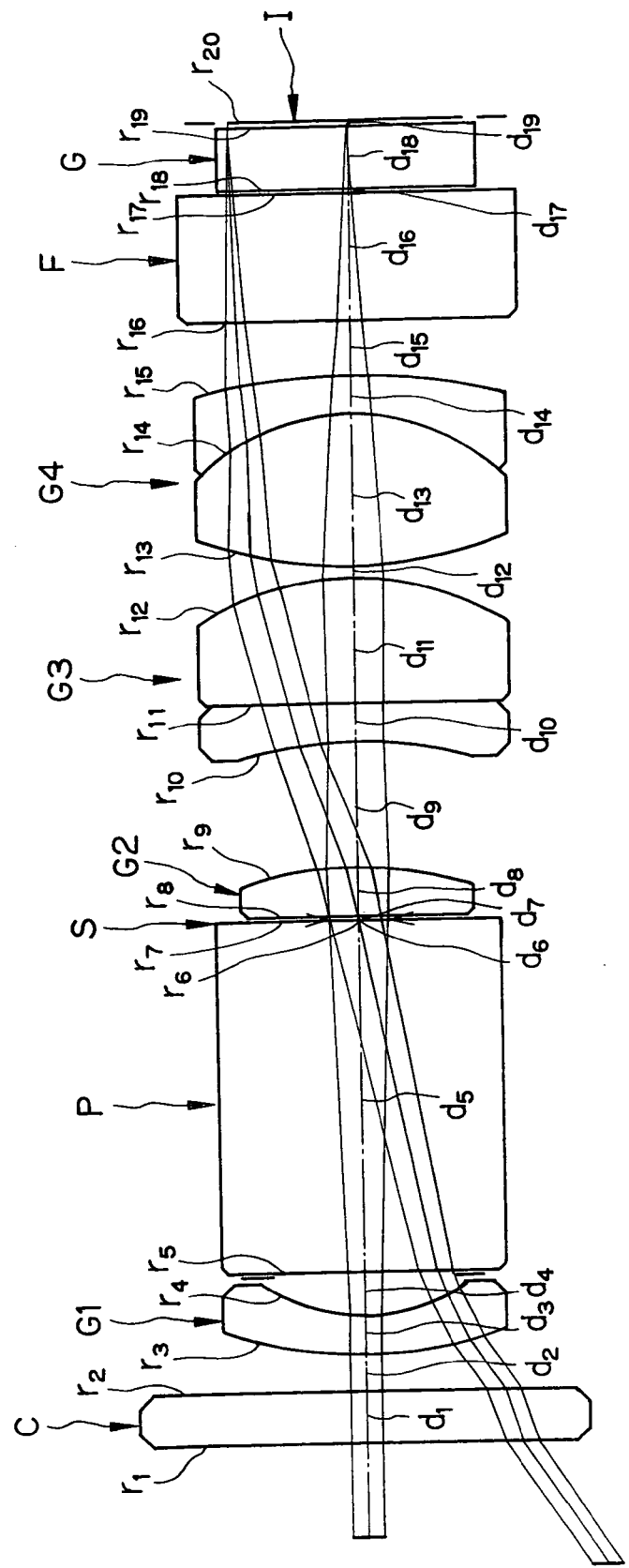
FIG. 18 is an optical path representation for the endoscopic objective optical system according to Example 12 of the invention.
Figure 19:
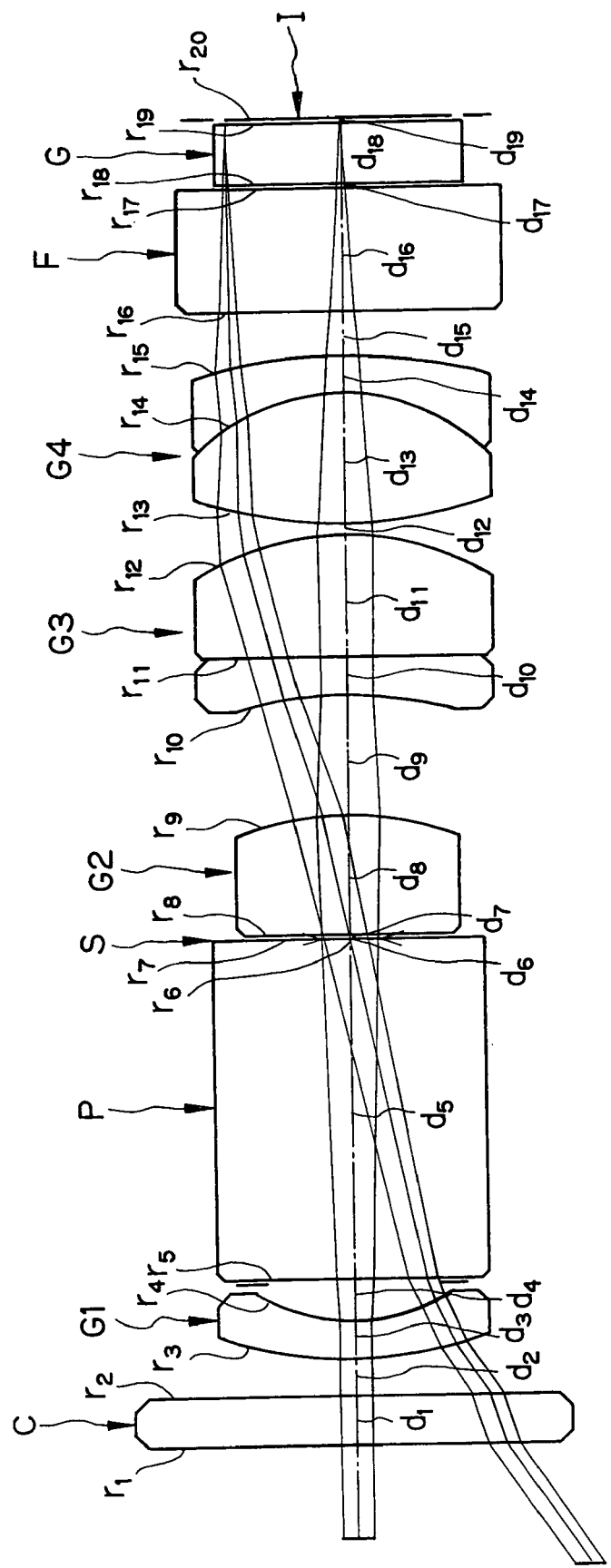
FIG. 19 is an optical path representation for the endoscopic objective optical system according to Example 13 of the invention.
Figure 20:
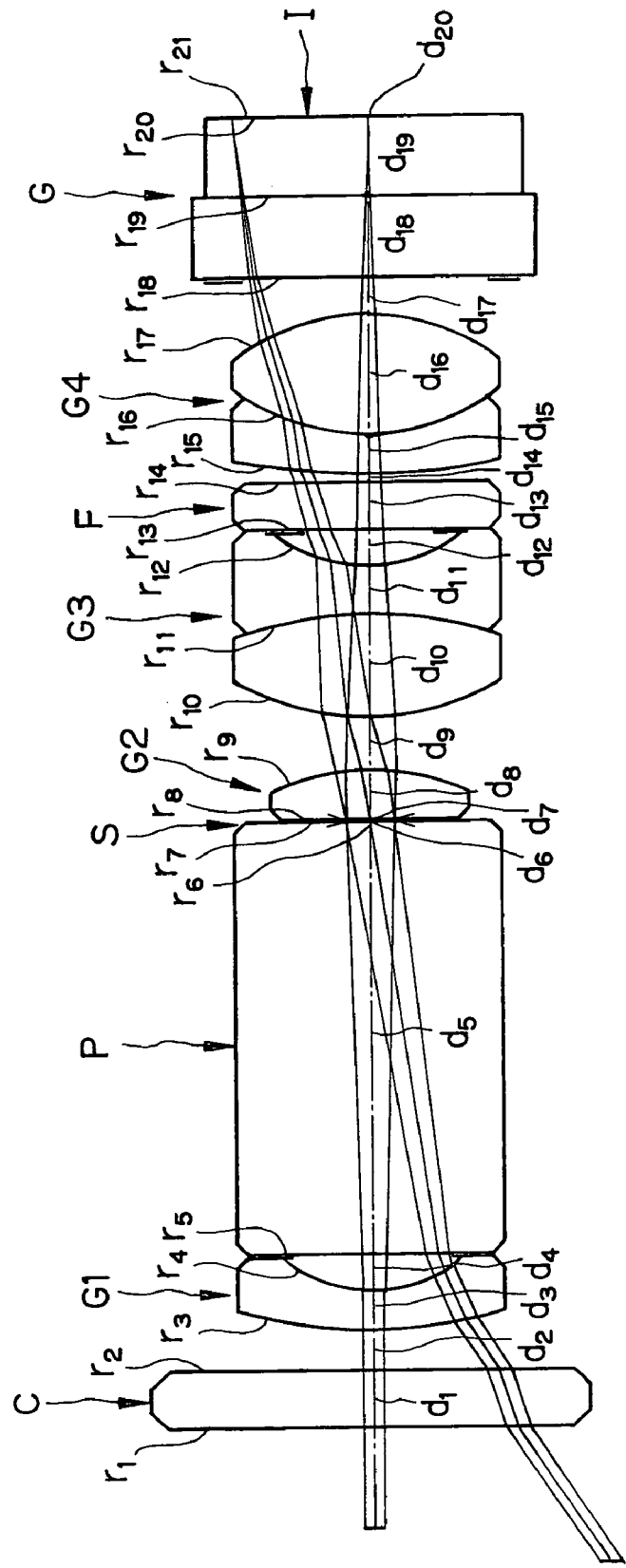
FIG. 20 is an optical path representation for the endoscopic objective optical system according to Example 14 of the invention.
Figure 21:
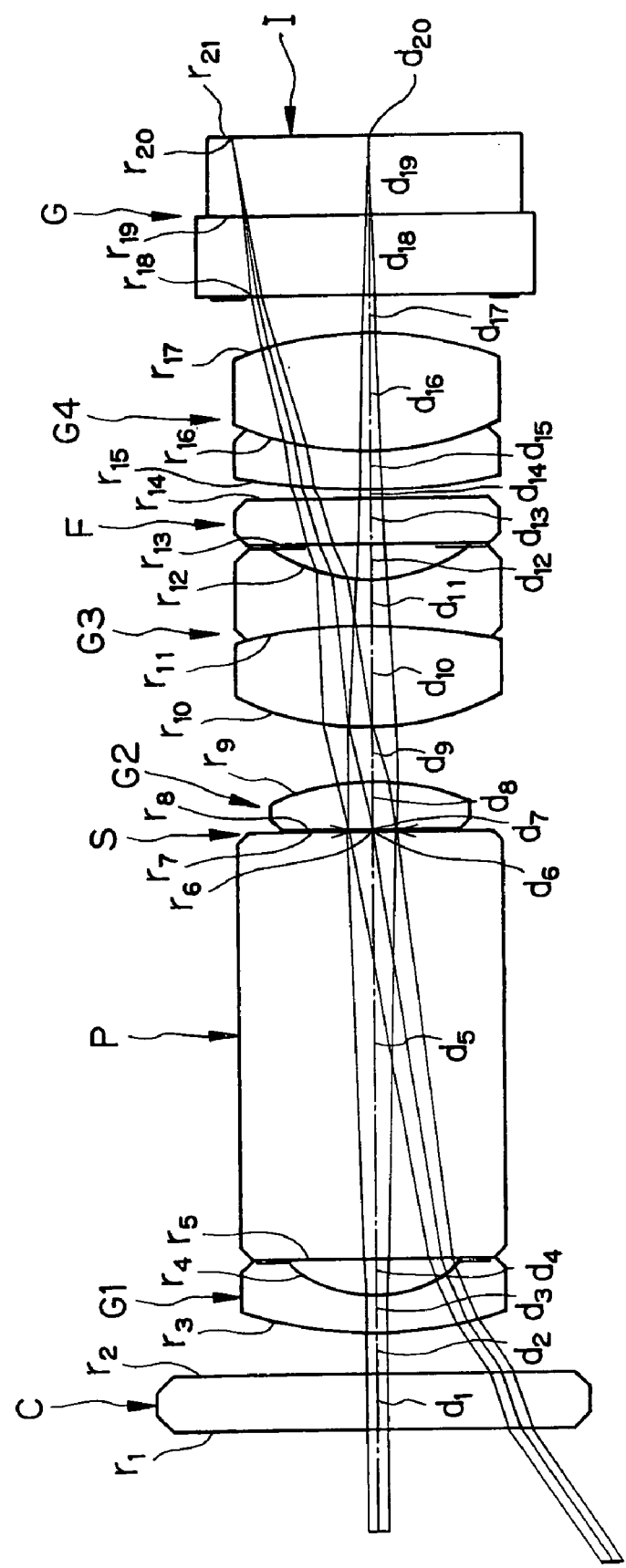
FIG. 21 is an optical path representation for the endoscopic objective optical system according to Example 15 of the invention.
Figure 39:
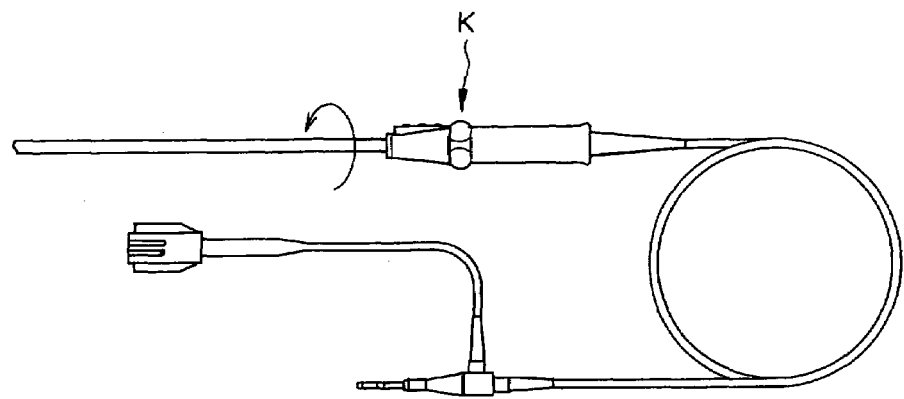
FIG. 39 is illustrative of the general configuration of a hard video endoscope.
Figure 40A:
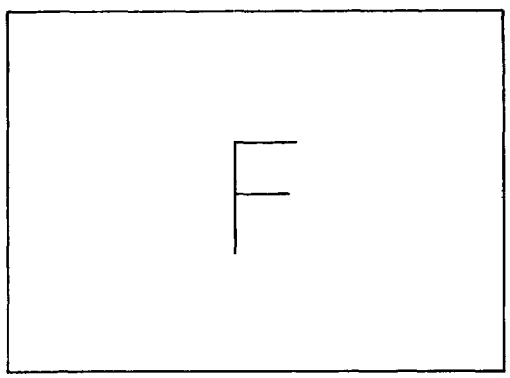
FIG. 40 is illustrative of the field, before (a) and after (b) rotation, of the hard video endoscope depicted in FIG. 39.
Figure 40B:
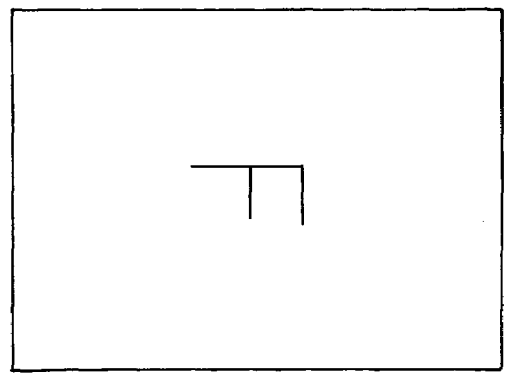
Figure 43:
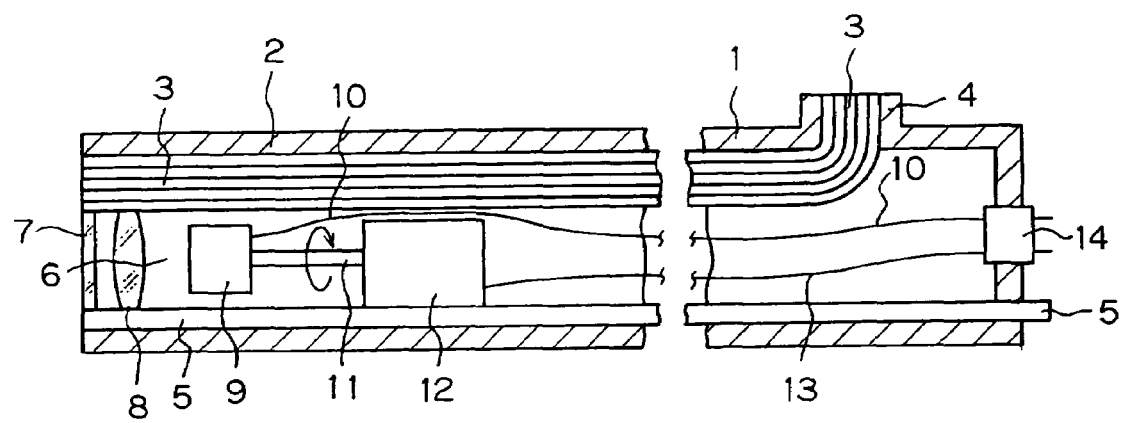
FIG. 43 is illustrative of a prior art example for rotating the image pickup plane of an optical system to make correction of image rotation.
Figure 44:
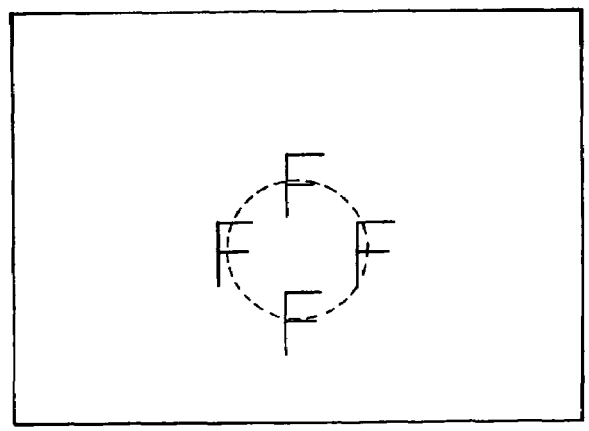
FIG. 44 is illustrative of a problem with the prior art example of FIG. 43.

Referring commonly to Examples 4, 5 and 6, the relations of the optical system to a mechanical frame are now explained. FIG. 11 is illustrative in section of the internal structure of the insert of a hard endoscope depicted in FIG. 39, and FIG. 12 is an enlarged view of its distal portion (indicated by an arrow in FIG. 11). A meniscus lens 21 (G1), a prism 22 (Pr) and a plano-convex lens 23 (G2) at the distal portion are incorporated in a frame 24 (hereinafter called a set 1). The set 1 is bonded to an outer tube 25 that is extended to an endoscope manipulation portion at which it is integrated with a manipulation knob K depicted in FIG. 39.

On the other hand, the third group and the fourth group are integrally incorporated in a frame 26, and engaged within, and bonded to, a frame 27 with a CCD built in it in an integral fashion (hereinafter called a set 2). The sets 1 and 2 are not bonded together; the set 1 is relatively rotated with the center of the longitudinal direction of the sets 1 and 2 and the center of the image pickup plane of the CCD as an axis. And then, the field can be turned in the desired field direction, as depicted in FIGS. 42(a), 42(b) and 42(c). The length of engagement of the frame 24 with the frame 26 here should preferably be as long as possible for the purpose of preventing their relative tilting.

Further, when there is a correction mechanism of field direction by rotation located, illumination means, too, must be rotatable following the field direction (FIG. 42). In the instant example, a light guide is built in the outer tube 25 in such a way as to be rotatable together with the front unit. The light guide is not fixed at the hand grip of the endoscope; that is, it is movable by rotation operation. The light guide is bendable at the distal portion of the endoscope in such a way as to illuminate the field direction.

EXAMPLES 7-15

FIGS. 13-21 are optical path representations for the endoscopic objective optical systems according to Examples 7-15, respectively, and FIGS. 28-36 are aberration diagrams, as in FIG. 22, for the endoscopic objective optical systems according to Examples 7-15.

Details of these examples are not explained, because Examples 7, 8 and 9 (FIGS. 13, 14 and 15) are much the same as in Example 2 (FIG. 5); Examples 10-13 (FIGS. 16-19) are much the same as in Example 1 (FIG. 4); and Examples 14 and 15 (FIGS. 20 and 21) are much the same as in Example 3 (FIG. 6).

While the endoscopic objective optical systems of Examples 1-15 are all standardized at a focal length of 1 mm for the purpose of brevity, it is understood that they should preferably have a focal length of about 1 to 3 mm and an image height of about 0.5 to 2 mm d in actual applications.

Regarding Examples 1 to 15 of the invention, lens data are now given below. Here, the symbols used with the lens data but not hereinbefore have the following meanings. F is the focal length of the whole optical system; $F_{NO}$ is an F-number; Ih is the maximum image height on the image plane; $2\omega$ is an angle of field; D is distortion at the maximum image height; $\alpha$ is the angle of incidence of chief rays on the maximum image height on the image plane; $r_1$, $r_2$ or the like is the radius of curvature of each lens surface; $d_1$, $d_2$ or the like is the spacing between adjacent lens surfaces; $n_{d1}$, $n_{d2}$ or the like is the d-line refractive index of each lens; $\nu_{d1}$, $\nu_{d2}$ or the like is the Abbe constant of each lens; $r_0$ is an object plane; and $d_0$ is an object distance.

EXAMPLE 1

| | | | |
|---|---|---|---|
| $r_0 = \infty$ (Object Plane) | $d_0 = 14.4568$ | | |
| $r_1 = \infty$ | $d_1 = 0.2754$ | $n_{d1} = 1.76820$ | $\nu_{d1} = 71.79$ |
| $r_2 = \infty$ | $d_2 = 0.2065$ | | |
| $r_3 = 2.5155$ | $d_3 = 0.2065$ | $n_{d2} = 1.88300$ | $\nu_{d2} = 40.76$ |
| $r_4 = 0.7993$ | $d_4 = 0.2341$ | | |
| $r_5 = \infty$ | $d_5 = 1.9276$ | $n_{d3} = 1.80610$ | $\nu_{d3} = 40.95$ |
| $r_6 = \infty$ | $d_6 = 0.0000$ | | |
| $r_7 = \infty$ (Stop) | $d_7 = 0.0207$ | | |
| $r_8 = \infty$ | $d_8 = 0.3442$ | $n_{d4} = 1.88300$ | $\nu_{d4} = 40.76$ |
| $r_9 = -1.4918$ | $d_9 = 0.6884$ | | |
| $r_{10} = -1.5696$ | $d_{10} = 0.2134$ | $n_{d5} = 1.84666$ | $\nu_{d5} = 23.78$ |
| $r_{11} = \infty$ | $d_{11} = 0.6884$ | $n_{d6} = 1.88300$ | $\nu_{d6} = 40.76$ |
| $r_{12} = -1.4918$ | $d_{12} = 0.0688$ | | |
| $r_{13} = 3.6989$ | $d_{13} = 0.8261$ | $n_{d7} = 1.51633$ | $\nu_{d7} = 64.14$ |
| $r_{14} = -1.0884$ | $d_{14} = 0.2065$ | $n_{d8} = 1.84666$ | $\nu_{d8} = 23.78$ |
| $r_{15} = -2.4102$ | $d_{15} = 0.3373$ | | |
| $r_{16} = \infty$ | $d_{16} = 1.1015$ | $n_{d9} = 1.51399$ | $\nu_{d9} = 75.00$ |
| $r_{17} = \infty$ | $d_{17} = 0.0138$ | $n_{d10} = 1.51000$ | $\nu_{d10} = 63.00$ |
| $r_{18} = \infty$ | $d_{18} = 0.3442$ | $n_{d11} = 1.51633$ | $\nu_{d11} = 64.14$ |
| $r_{19} = \infty$ | $d_{19} = 0.0207$ | | |
| $r_{20} = \infty$ (Image plane) | | | |
| F = 1.00 | | | |
| $F_{NO} = 6.058$ | | | |
| Ih = 0.627 | | | |
| $2\omega$ (°) = 69.425 | | | |
| D (%) = −9.475 | | | |
| $\alpha$ (°) = 3.038 | | | |

EXAMPLE 2

| | | | |
|---|---|---|---|
| $r_0 = \infty$ (Object Plane) | $d_0 = 14.9395$ | | |
| $r_1 = \infty$ | $d_1 = 0.2988$ | $n_{d1} = 1.76820$ | $\nu_{d1} = 71.79$ |
| $r_2 = \infty$ | $d_2 = 0.2134$ | | |
| $r_3 = 4.5420$ | $d_3 = 0.1921$ | $n_{d2} = 1.88300$ | $\nu_{d2} = 40.76$ |
| $r_4 = 0.8204$ | $d_4 = 0.1921$ | | |
| $r_5 = \infty$ | $d_5 = 2.5610$ | $n_{d3} = 1.88300$ | $\nu_{d3} = 40.76$ |
| $r_6 = \infty$ (Stop) | $d_6 = 0.0128$ | | |
| $r_7 = \infty$ | $d_7 = 0.4695$ | $n_{d4} = 1.72916$ | $\nu_{d4} = 54.68$ |
| $r_8 = -1.7253$ | $d_8 = 0.2988$ | | |
| $r_9 = 1.6404$ | $d_9 = 0.5976$ | $n_{d5} = 1.88300$ | $\nu_{d5} = 40.76$ |
| $r_{10} = \infty$ | $d_{10} = 0.2134$ | | |
| $r_{11} = -1.5832$ | $d_{11} = 0.6701$ | $n_{d6} = 1.75520$ | $\nu_{d6} = 27.51$ |
| $r_{12} = 1.5832$ | $d_{12} = 0.1067$ | | |
| $r_{13} = \infty$ | $d_{13} = 0.5976$ | $n_{d7} = 1.88300$ | $\nu_{d7} = 40.76$ |
| $r_{14} = -1.6404$ | $d_{14} = 0.0427$ | | |
| $r_{15} = 2.4889$ | $d_{15} = 0.2134$ | $n_{d8} = 1.84666$ | $\nu_{d8} = 23.78$ |
| $r_{16} = 1.0321$ | $d_{16} = 0.6360$ | $n_{d9} = 1.48749$ | $\nu_{d9} = 70.23$ |

-continued

| | | | |
|---|---|---|---|
| $r_{17} = -2.8462$ | $d_{17} = 0.2220$ | | |
| $r_{18} = \infty$ | $d_{18} = 0.6829$ | $n_{d10} = 1.51400$ | $\nu_{d10} = 75.00$ |
| $r_{19} = \infty$ | $d_{19} = 0.0085$ | $n_{d11} = 1.51000$ | $\nu_{d11} = 63.00$ |
| $r_{20} = \infty$ | $d_{20} = 0.2134$ | $n_{d12} = 1.51633$ | $\nu_{d12} = 64.14$ |
| $r_{21} = \infty$ | $d_{21} = 0.0128$ | | |
| $r_{22} = \infty$ (Image plane) | | | |
| $F = 1.00$ | | | |
| $F_{NO} = 7.925$ | | | |
| $Ih = 0.643$ | | | |
| $2\omega$ (°) = 69.016 | | | |
| $D$ (%) = −6.353 | | | |
| $\alpha$ (°) = 5.468 | | | |

EXAMPLE 3

| | | | |
|---|---|---|---|
| $r_0 = \infty$ (Object Plane) | $d_0 = 14.5912$ | | |
| $r_1 = \infty$ | $d_1 = 0.2918$ | $n_{d1} = 1.76820$ | $\nu_{d1} = 71.79$ |
| $r_2 = \infty$ | $d_2 = 0.2084$ | | |
| $r_3 = 2.7707$ | $d_3 = 0.2084$ | $n_{d2} = 1.88300$ | $\nu_{d2} = 40.76$ |
| $r_4 = 0.7158$ | $d_4 = 0.1751$ | | |
| $r_5 = \infty$ | $d_5 = 0.0125$ | | |
| $r_6 = \infty$ | $d_6 = 2.2929$ | $n_{d3} = 1.88300$ | $\nu_{d3} = 40.76$ |
| $r_7 = \infty$ (Stop) | $d_7 = 0.0125$ | | |
| $r_8 = \infty$ | $d_8 = 0.3669$ | $n_{d4} = 1.78800$ | $\nu_{d4} = 47.37$ |
| $r_9 = -1.3111$ | $d_9 = 0.2918$ | | |
| $r_{10} = 1.4770$ | $d_{10} = 0.5420$ | $n_{d5} = 1.88300$ | $\nu_{d5} = 40.76$ |
| $r_{11} = -2.5901$ | $d_{11} = 0.2501$ | $n_{d6} = 1.74077$ | $\nu_{d6} = 27.79$ |
| $r_{12} = 0.8288$ | $d_{12} = 0.1876$ | | |
| $r_{13} = \infty$ | $d_{13} = 0.2501$ | $n_{d7} = 1.51800$ | $\nu_{d7} = 74.60$ |
| $r_{14} = \infty$ | $d_{14} = 0.0417$ | | |
| $r_{15} = 3.2188$ | $d_{15} = 0.2084$ | $n_{d8} = 1.84666$ | $\nu_{d8} = 23.78$ |
| $r_{16} = 1.2428$ | $d_{16} = 0.6253$ | $n_{d9} = 1.51633$ | $\nu_{d9} = 64.14$ |
| $r_{17} = -1.4479$ | $d_{17} = 0.1876$ | | |
| $r_{18} = \infty$ | $d_{18} = 0.4211$ | $n_{d10} = 1.51633$ | $\nu_{d10} = 64.14$ |
| $r_{19} = \infty$ | $d_{19} = 0.4169$ | $n_{d11} = 1.61350$ | $\nu_{d11} = 50.20$ |
| $r_{20} = \infty$ | $d_{20} = 0.0000$ | | |
| $r_{21} = \infty$ (Image plane) | | | |
| $F = 1.00$ | | | |
| $F_{NO} = 8.925$ | | | |
| $Ih = 0.679$ | | | |
| $2\omega$ (°) = 72.785 | | | |
| $D$ (%) = −8.913 | | | |
| $\alpha$ (°) = 11.358 | | | |

EXAMPLE 4

| | | | |
|---|---|---|---|
| $r_0 = \infty$ (Object Plane) | $d_0 = 14.4592$ | | |
| $r_1 = \infty$ | $d_1 = 0.2754$ | $n_{d1} = 1.76820$ | $\nu_{d1} = 71.79$ |
| $r_2 = \infty$ | $d_2 = 0.2066$ | | |
| $r_3 = 2.5159$ | $d_3 = 0.2066$ | $n_{d2} = 1.88300$ | $\nu_{d2} = 40.76$ |
| $r_4 = 0.7994$ | $d_4 = 0.2341$ | | |
| $r_5 = \infty$ | $d_5 = 0.3305$ | $n_{d3} = 1.88300$ | $\nu_{d3} = 40.76$ |
| $r_6 = \infty$ | $d_6 = 0.0392$ | | |
| $r_7 = \infty$ | $d_7 = 0.4462$ | $n_{d4} = 1.88300$ | $\nu_{d4} = 40.76$ |
| $r_8 = \infty$ | $d_8 = 0.6094$ | $n_{d5} = 1.88300$ | $\nu_{d5} = 40.76$ |
| $r_9 = \infty$ | $d_9 = 0.5508$ | $n_{d6} = 1.88300$ | $\nu_{d6} = 40.76$ |
| $r_{10} = \infty$ (Stop) | $d_{10} = 0.0207$ | | |
| $r_{11} = \infty$ | $d_{11} = 0.3443$ | $n_{d7} = 1.88300$ | $\nu_{d7} = 40.76$ |
| $r_{12} = -1.4921$ | $d_{12} = 0.6885$ | | |
| $r_{13} = -1.5699$ | $d_{13} = 0.2134$ | $n_{d8} = 1.84666$ | $\nu_{d8} = 23.78$ |
| $r_{14} = \infty$ | $d_{14} = 0.6885$ | $n_{d9} = 1.88300$ | $\nu_{d9} = 40.76$ |
| $r_{15} = -1.4921$ | $d_{15} = 0.0689$ | | |
| $r_{16} = 3.6995$ | $d_{16} = 0.8262$ | $n_{d10} = 1.51633$ | $\nu_{d10} = 64.14$ |
| $r_{17} = -1.0886$ | $d_{17} = 0.2066$ | $n_{d11} = 1.84666$ | $\nu_{d11} = 23.78$ |
| $r_{18} = -2.4106$ | $d_{18} = 0.3374$ | | |
| $r_{19} = \infty$ | $d_{19} = 1.1017$ | $n_{d12} = 1.51399$ | $\nu d_{12} = 75.00$ |
| $r_{20} = \infty$ | $d_{20} = 0.0138$ | $n_{d13} = 1.51000$ | $\nu_{d13} = 63.00$ |

-continued

| | | | |
|---|---|---|---|
| $r_{21} = \infty$ | $d_{21} = 0.3443$ | $n_{d14} = 1.51633$ | $\nu_{d14} = 64.14$ |
| $r_{22} = \infty$ | $d_{22} = 0.0207$ | | |
| $r_{23} = \infty$ (Image plane) | | | |
| $F = 1.00$ | | | |
| $F_{NO} = 6.058$ | | | |
| $Ih = 0.627$ | | | |
| $2\omega$ (°) = 69.406 | | | |
| $D$ (%) = −9.428 | | | |
| $\alpha$ (°) = 3.037 | | | |

EXAMPLE 5

| | | | |
|---|---|---|---|
| $r_0 = \infty$ (Object Plane) | $d_0 = 14.9395$ | | |
| $r_1 = \infty$ | $d_1 = 0.2988$ | $n_{d1} = 1.76820$ | $\nu_{d1} = 71.79$ |
| $r_2 = \infty$ | $d_2 = 0.2134$ | | |
| $r_3 = 4.5420$ | $d_3 = 0.1921$ | $n_{d2} = 1.88300$ | $\nu_{d2} = 40.76$ |
| $r_4 = 0.8204$ | $d_4 = 0.1921$ | | |
| $r_5 = \infty$ | $d_5 = 0.7022$ | $n_{d3} = 1.88300$ | $\nu_{d3} = 40.76$ |
| $r_6 = \infty$ | $d_6 = 0.4930$ | $n_{d4} = 1.88300$ | $\nu_{d4} = 40.76$ |
| $r_7 = \infty$ | $d_7 = 0.8537$ | $n_{d5} = 1.88300$ | $\nu_{d5} = 40.76$ |
| $r_8 = \infty$ | $d_8 = 0.5122$ | $n_{d6} = 1.88300$ | $\nu_{d6} = 40.76$ |
| $r_9 = \infty$ (Stop) | $d_9 = 0.0128$ | | |
| $r_{10} = \infty$ | $d_{10} = 0.4695$ | $n_{d7} = 1.72916$ | $\nu_{d7} = 54.68$ |
| $r_{11} = -1.7253$ | $d_{11} = 0.2988$ | | |
| $r_{12} = 1.6404$ | $d_{12} = 0.5976$ | $n_{d8} = 1.88300$ | $\nu_{d8} = 40.76$ |
| $r_{13} = \infty$ | $d_{13} = 0.2134$ | | |
| $r_{14} = -1.5832$ | $d_{14} = 0.6701$ | $n_{d9} = 1.75520$ | $\nu_{d9} = 27.51$ |
| $r_{15} = 1.5832$ | $d_{15} = 0.1067$ | | |
| $r_{16} = \infty$ | $d_{16} = 0.5976$ | $n_{d10} = 1.88300$ | $\nu_{d10} = 40.76$ |
| $r_{17} = -1.6404$ | $d_{17} = 0.0427$ | | |
| $r_{18} = 2.4889$ | $d_{18} = 0.2134$ | $n_{d11} = 1.84666$ | $\nu_{d11} = 23.78$ |
| $r_{19} = 1.0321$ | $d_{19} = 0.6360$ | $n_{d12} = 1.48749$ | $\nu_{d12} = 70.23$ |
| $r_{20} = -2.8462$ | $d_{20} = 0.2220$ | | |
| $r_{21} = \infty$ | $d_{21} = 0.6829$ | $n_{d13} = 1.51400$ | $\nu_{d13} = 75.00$ |
| $r_{22} = \infty$ | $d_{22} = 0.0085$ | $n_{d14} = 1.51000$ | $\nu_{d14} = 63.00$ |
| $r_{23} = \infty$ | $d_{23} = 0.2134$ | $n_{d15} = 1.51633$ | $\nu_{d15} = 64.14$ |
| $r_{24} = \infty$ | $d_{24} = 0.0128$ | | |
| $r_{25} = \infty$ (Image plane) | | | |
| $F = 1.00$ | | | |
| $F_{NO} = 7.925$ | | | |
| $Ih = 0.643$ | | | |
| $2\omega$ (°) = 69.016 | | | |
| $D$ (%) = −6.353 | | | |
| $\alpha$ (°) = 5.468 | | | |

EXAMPLE 6

| | | | |
|---|---|---|---|
| $r_0 = \infty$ (Object Plane) | $d_0 = 20.8169$ | | |
| $r_1 = \infty$ | $d_1 = 0.2914$ | $n_{d1} = 1.76820$ | $\nu_{d1} = 71.79$ |
| $r_2 = \infty$ | $d_2 = 0.2082$ | | |
| $r_3 = 2.7670$ | $d_3 = 0.2082$ | $n_{d2} = 1.88300$ | $\nu_{d2} = 40.76$ |
| $r_4 = 0.7149$ | $d_4 = 0.1874$ | | |
| $r_5 = \infty$ | $d_5 = 0.6245$ | $n_{d3} = 1.88300$ | $\nu_{d3} = 40.76$ |
| $r_6 = \infty$ | $d_6 = 0.4413$ | $n_{d4} = 1.88300$ | $\nu_{d4} = 40.76$ |
| $r_7 = \infty$ | $d_7 = 0.7619$ | $n_{d5} = 1.88300$ | $\nu_{d5} = 40.76$ |
| $r_8 = \infty$ | $d_8 = 0.4580$ | $n_{d6} = 1.88300$ | $\nu_{d6} = 40.76$ |
| $r_9 = \infty$ (Stop) | $d_9 = 0.0125$ | | |
| $r_{10} = \infty$ | $d_{10} = 0.3664$ | $n_{d7} = 1.78800$ | $\nu_{d7} = 47.37$ |
| $r_{11} = -1.3094$ | $d_{11} = 0.2914$ | | |
| $r_{12} = 1.4751$ | $d_{12} = 0.5412$ | $n_{d8} = 1.88300$ | $\nu_{d8} = 40.76$ |
| $r_{13} = -2.5867$ | $d_{13} = 0.2498$ | $n_{d9} = 1.74077$ | $\nu_{d9} = 27.79$ |
| $r_{14} = 0.8277$ | $d_{14} = 0.1874$ | | |
| $r_{15} = \infty$ | $d_{15} = 0.2498$ | $n_{d10} = 1.51800$ | $\nu_{d10} = 74.60$ |
| $r_{16} = \infty$ | $d_{16} = 0.0416$ | | |
| $r_{17} = 3.2145$ | $d_{17} = 0.2082$ | $n_{d11} = 1.84666$ | $\nu_{d11} = 23.78$ |
| $r_{18} = 1.2411$ | $d_{18} = 0.6245$ | $n_{d12} = 1.51633$ | $\nu_{d12} = 64.14$ |
| $r_{19} = -1.4459$ | $d_{19} = 0.1874$ | | |

-continued

| | | | |
|---|---|---|---|
| $r_{20} = \infty$ | $d_{20} = 0.4205$ | $n_{d13} = 1.51633$ | $\nu_{d13} = 64.14$ |
| $r_{21} = \infty$ | $d_{21} = 0.4163$ | $n_{d14} = 1.61350$ | $\nu_{d14} = 50.20$ |
| $r_{22} = \infty$ | $d_{22} = 0.0000$ | | |
| $r_{23} = \infty$ (Image plane) | | | |
| F = 1.00 | | | |
| $F_{NO} = 8.885$ | | | |
| Ih = 0.678 | | | |
| $2\omega$ (°) = 72.715 | | | |
| D (%) = −8.621 | | | |
| $\alpha$ (°) = 11.358 | | | |

EXAMPLE 7

| | | | |
|---|---|---|---|
| $r_0 = \infty$ (Object Plane) | $d_0 = 14.6532$ | | |
| $r_1 = \infty$ | $d_1 = 0.2931$ | $n_{d1} = 1.76820$ | $\nu_{d1} = 71.79$ |
| $r_2 = \infty$ | $d_2 = 0.2093$ | | |
| $r_3 = 4.3378$ | $d_3 = 0.1884$ | $n_{d2} = 1.88300$ | $\nu_{d2} = 40.76$ |
| $r_4 = 0.8191$ | $d_4 = 0.1884$ | | |
| $r_5 = \infty$ | $d_5 = 2.5120$ | $n_{d3} = 1.88300$ | $\nu_{d3} = 40.76$ |
| $r_6 = \infty$ (Stop) | $d_6 = 0.0126$ | | |
| $r_7 = \infty$ | $d_7 = 0.4605$ | $n_{d4} = 1.72916$ | $\nu_{d4} = 54.68$ |
| $r_8 = -1.6417$ | $d_8 = 0.2931$ | | |
| $r_9 = 1.5032$ | $d_9 = 0.4187$ | $n_{d5} = 1.77250$ | $\nu_{d5} = 49.60$ |
| $r_{10} = \infty$ | $d_{10} = 0.2093$ | | |
| $r_{11} = -3.3253$ | $d_{11} = 0.4187$ | $n_{d6} = 1.75520$ | $\nu_{d6} = 27.51$ |
| $r_{12} = 1.9014$ | $d_{12} = 0.1758$ | | |
| $r_{13} = \infty$ | $d_{13} = 0.5382$ | $n_{d7} = 1.72916$ | $\nu_{d7} = 54.68$ |
| $r_{14} = -2.1251$ | $d_{14} = 0.0837$ | | |
| $r_{15} = 6.2758$ | $d_{15} = 0.6238$ | $n_{d8} = 1.51823$ | $\nu_{d8} = 58.90$ |
| $r_{16} = -0.7299$ | $d_{16} = 0.2093$ | $n_{d9} = 1.71736$ | $\nu_{d9} = 29.52$ |
| $r_{17} = -2.9131$ | $d_{17} = 0.0937$ | | |
| $r_{18} = \infty$ | $d_{18} = 0.6699$ | $n_{d10} = 1.51400$ | $\nu_{d10} = 75.00$ |
| $r_{19} = \infty$ | $d_{19} = 0.0084$ | $n_{d10} = 1.51000$ | $\nu_{d11} = 63.00$ |
| $r_{20} = \infty$ | $d_{20} = 0.2093$ | $n_{d12} = 1.51633$ | $\nu_{d12} = 64.14$ |
| $r_{21} = \infty$ | $d_{21} = 0.0126$ | | |
| $r_{22} = \infty$ (Image plane) | | | |
| F = 1.00 | | | |
| $F_{NO} = 4.634$ | | | |
| Ih = 0.631 | | | |
| $2\omega$ (°) = 68.610 | | | |
| D (%) = −8.317 | | | |
| $\alpha$ (°) = 8.899 | | | |

EXAMPLE 8

| | | | |
|---|---|---|---|
| $r_0 = \infty$ (Object Plane) | $d_0 = 14.4134$ | | |
| $r_1 = \infty$ | $d_1 = 0.2883$ | $n_{d1} = 1.76820$ | $\nu_{d1} = 71.79$ |
| $r_2 = \infty$ | $d_2 = 0.2059$ | | |
| $r_3 = 5.1056$ | $d_3 = 0.1853$ | $n_{d2} = 1.88300$ | $\nu_{d2} = 40.76$ |
| $r_4 = 0.7598$ | $d_4 = 0.1854$ | | |
| $r_5 = \infty$ | $d_5 = 2.4709$ | $n_{d3} = 1.88300$ | $\nu_{d3} = 40.76$ |
| $r_6 = \infty$ (Stop) | $d_6 = 0.0124$ | | |
| $r_7 = \infty$ | $d_7 = 0.2059$ | $n_{d4} = 1.72916$ | $\nu_{d4} = 54.68$ |
| $r_8 = -1.4755$ | $d_8 = 0.2883$ | | |
| $r_9 = 1.5871$ | $d_9 = 0.4375$ | $n_{d5} = 1.77250$ | $\nu_{d5} = 49.60$ |
| $r_{10} = \infty$ | $d_{10} = 0.2059$ | | |
| $r_{11} = -4.0713$ | $d_{11} = 0.4118$ | $n_{d6} = 1.75520$ | $\nu_{d6} = 27.51$ |
| $r_{12} = 1.8879$ | $d_{12} = 0.1730$ | | |
| $r_{13} = \infty$ | $d_{13} = 0.5294$ | $n_{d7} = 1.72916$ | $\nu_{d7} = 54.68$ |
| $r_{14} = -2.1561$ | $d_{14} = 0.0824$ | | |
| $r_{15} = 7.1108$ | $d_{15} = 0.6136$ | $n_{d8} = 1.51823$ | $\nu_{d8} = 58.90$ |
| $r_{16} = -0.7292$ | $d_{16} = 0.2059$ | $n_{d9} = 1.71736$ | $\nu_{d9} = 29.52$ |
| $r_{17} = -3.4414$ | $d_{17} = 0.1140$ | | |
| $r_{18} = \infty$ | $d_{18} = 0.6589$ | $n_{d10} = 1.51400$ | $\nu_{d10} = 75.00$ |
| $r_{19} = \infty$ | $d_{19} = 0.0082$ | $n_{d11} = 1.51000$ | $\nu_{d11} = 63.00$ |
| $r_{20} = \infty$ | $d_{20} = 0.2059$ | $n_{d12} = 1.51633$ | $\nu_{d12} = 64.14$ |
| $r_{21} = \infty$ | $d_{21} = 0.0124$ | | |
| $r_{22} = \infty$ (Image plane) | | | |
| F = 1.00 | | | |
| $F_{NO} = 5.060$ | | | |
| Ih = 0.621 | | | |
| $2\omega$ (°) = 67.792 | | | |
| D (%) = −8.808 | | | |
| $\alpha$ (°) = 10.508 | | | |

EXAMPLE 9

| | | | |
|---|---|---|---|
| $r_0 = \infty$ (Object Plane) | $d_0 = 14.8973$ | | |
| $r_1 = \infty$ | $d_1 = 0.2979$ | $n_{d1} = 1.76820$ | $\nu_{d1} = 71.79$ |
| $r_2 = \infty$ | $d_2 = 0.2128$ | | |
| $r_3 = 3.0953$ | $d_3 = 0.1915$ | $n_{d2} = 1.88300$ | $\nu_{d2} = 40.76$ |
| $r_4 = 0.9805$ | $d_4 = 0.1916$ | | |
| $r_5 = \infty$ | $d_5 = 2.3800$ | $n_{d3} = 1.88300$ | $\nu_{d3} = 40.76$ |
| $r_6 = \infty$ (Stop) | $d_6 = 0.0128$ | | |
| $r_7 = \infty$ | $d_7 = 0.6385$ | $n_{d4} = 1.72916$ | $\nu_{d4} = 54.68$ |
| $r_8 = -1.8937$ | $d_8 = 0.2979$ | | |
| $r_9 = 2.0182$ | $d_9 = 0.4522$ | $n_{d5} = 1.77250$ | $\nu_{d5} = 49.60$ |
| $r_{10} = \infty$ | $d_{10} = 0.2128$ | | |
| $r_{11} = -2.5538$ | $d_{11} = 0.4256$ | $n_{d6} = 1.75520$ | $\nu_{d6} = 27.51$ |
| $r_{12} = 3.5902$ | $d_{12} = 0.1787$ | | |
| $r_{13} = \infty$ | $d_{13} = 0.5472$ | $n_{d7} = 1.72916$ | $\nu_{d7} = 54.68$ |
| $r_{14} = -1.3625$ | $d_{14} = 0.0851$ | | |
| $r_{15} = 3.3306$ | $d_{15} = 0.6342$ | $n_{d8} = 1.51823$ | $\nu_{d8} = 58.90$ |
| $r_{16} = -0.7834$ | $d_{16} = 0.2128$ | $n_{d9} = 1.71736$ | $\nu_{d9} = 29.52$ |
| $r_{17} = -5.2313$ | $d_{17} = 0.1146$ | | |
| $r_{18} = \infty$ | $d_{18} = 0.6810$ | $n_{d10} = 1.51400$ | $\nu_{d10} = 75.00$ |
| $r_{19} = \infty$ | $d_{19} = 0.0085$ | $n_{d11} = 1.51000$ | $\nu_{d11} = 63.00$ |
| $r_{20} = \infty$ | $d_{20} = 0.2128$ | $n_{d12} = 1.51633$ | $\nu_{d12} = 64.14$ |
| $r_{21} = \infty$ | $d_{21} = 0.0128$ | | |
| $r_{22} = \infty$ (Image plane) | | | |
| F = 1.00 | | | |
| $F_{NO} = 8.885$ | | | |
| Ih = 0.641 | | | |
| $2\omega$ (°) = 68.037 | | | |
| D (%) = −4.880 | | | |
| $\alpha$ (°) = 4.876 | | | |

EXAMPLE 10

| | | | |
|---|---|---|---|
| $r_0 = \infty$ (Object Plane) | $d_0 = 14.2337$ | | |
| $r_1 = \infty$ | $d_1 = 0.2711$ | $n_{d1} = 1.76820$ | $\nu_{d1} = 71.79$ |
| $r_2 = \infty$ | $d_2 = 0.2033$ | | |
| $r_3 = 2.1480$ | $d_3 = 0.2033$ | $n_{d2} = 1.88300$ | $\nu_{d2} = 40.76$ |
| $r_4 = 0.8544$ | $d_4 = 0.2304$ | | |
| $r_5 = \infty$ | $d_5 = 1.8978$ | $n_{d3} = 1.80610$ | $\nu_{d3} = 40.95$ |
| $r_6 = \infty$ | $d_6 = 0.0000$ | | |
| $r_7 = \infty$ (Stop) | $d_7 = 0.0203$ | | |
| $r_8 = \infty$ | $d_8 = 0.3389$ | $n_{d4} = 1.88300$ | $\nu_{d4} = 40.76$ |
| $r_9 = -1.7259$ | $d_9 = 0.6778$ | | |
| $r_{10} = -2.0622$ | $d_{10} = 0.2101$ | $n_{d5} = 1.84666$ | $\nu_{d5} = 23.78$ |
| $r_{11} = \infty$ | $d_{11} = 0.6778$ | $n_{d6} = 1.88300$ | $\nu_{d6} = 40.76$ |
| $r_{12} = -1.5631$ | $d_{12} = 0.0678$ | | |
| $r_{13} = 2.2179$ | $d_{13} = 0.8134$ | $n_{d7} = 1.51633$ | $\nu_{d7} = 64.14$ |
| $r_{14} = -1.2429$ | $d_{14} = 0.2033$ | $n_{d8} = 1.84666$ | $\nu_{d8} = 23.78$ |
| $r_{15} = -3.6966$ | $d_{15} = 0.1105$ | | |
| $r_{16} = \infty$ | $d_{16} = 1.0845$ | $n_{d9} = 1.51399$ | $\nu_{d9} = 75.00$ |
| $r_{17} = \infty$ | $d_{17} = 0.0136$ | $n_{d10} = 1.51000$ | $\nu_{d10} = 63.00$ |
| $r_{18} = \infty$ | $d_{18} = 0.3389$ | $n_{d11} = 1.51633$ | $\nu_{d11} = 64.14$ |
| $r_{19} = \infty$ | $d_{19} = 0.0203$ | | |
| $r_{20} = \infty$ (Image plane) | | | |
| F = 1.00 | | | |
| $F_{NO} = 5.522$ | | | |

-continued

Ih = 0.617
2ω (°) = 68.239
D (%) = −8.977
α (°) = 3.029

EXAMPLE 11

| | | | |
|---|---|---|---|
| $r_0$ ∞ (Object Plane) | $d_0$ = 14.2786 | | |
| $r_1$ = ∞ | $d_1$ = 0.2720 | $n_{d1}$ = 1.76820 | $v_{d1}$ = 71.79 |
| $r_2$ = ∞ | $d_2$ = 0.2040 | | |
| $r_3$ = 2.2075 | $d_3$ = 0.2040 | $n_{d2}$ = 1.88300 | $v_{d2}$ = 40.76 |
| $r_4$ = 0.9147 | $d_4$ = 0.2312 | | |
| $r_5$ = 1.9038 | $d_5$ = 1.9038 | $n_{d3}$ = 1.80610 | $v_{d3}$ = 40.95 |
| $r_6$ = ∞ | $d_6$ = 0.0000 | | |
| $r_7$ = ∞ (Stop) | $d_7$ = 0.0204 | | |
| $r_8$ = ∞ | $d_8$ = 0.6799 | $n_{d4}$ = 1.88300 | $v_{d4}$ = 40.76 |
| $r_9$ = −1.5496 | $d_9$ = 0.6799 | | |
| $r_{10}$ = −1.9256 | $d_{10}$ = 0.2108 | $n_{d5}$ = 1.84666 | $v_{d5}$ = 23.78 |
| $r_{11}$ = ∞ | $d_{11}$ = 0.6799 | $n_{d6}$ = 1.88300 | $v_{d6}$ = 40.76 |
| $r_{12}$ = −1.5467 | $d_{12}$ = 0.0680 | | |
| $r_{13}$ = 2.4495 | $d_{13}$ = 0.7354 | $n_{d7}$ = 1.51633 | $v_{d7}$ = 64.14 |
| $r_{14}$ = −1.1536 | $d_{14}$ = 0.2040 | $n_{d8}$ = 1.84666 | $v_{d8}$ = 23.78 |
| $r_{15}$ = −3.4560 | $d_{15}$ = 0.2473 | | |
| $r_{16}$ = ∞ | $d_{16}$ = 0.6799 | $n_{d9}$ = 1.51399 | $v_{d9}$ = 75.00 |
| $r_{17}$ = ∞ | $d_{17}$ = 0.0136 | $n_{d10}$ = 1.51000 | $v_{d10}$ = 63.00 |
| $r_{18}$ = ∞ | $d_{18}$ = 0.3400 | $n_{d11}$ = 1.51633 | $v_{d11}$ = 64.14 |
| $r_{19}$ = ∞ | $d_{19}$ = 0.0204 | | |
| $r_{20}$ = ∞ (Image plane) | | | |

F = 1.00
$F_{NO}$ = 5.275
Ih = 0.619
2ω (°) = 68.000
D (%) = −7.990
α (°) = 1.974

EXAMPLE 12

| | | | |
|---|---|---|---|
| $r_0$ = ∞ (Object Plane) | $d_0$ = 14.4872 | | |
| $r_1$ = ∞ | $d_1$ = 0.2759 | $n_{d1}$ = 1.76820 | $v_{d1}$ = 71.79 |
| $r_2$ = ∞ | $d_2$ = 0.2070 | | |
| $r_3$ = 2.2610 | $d_3$ = 0.2070 | $n_{d2}$ = 1.88300 | $v_{d2}$ = 40.76 |
| $r_4$ = 0.9179 | $d_4$ = 0.2346 | | |
| $r_5$ = 1.9316 | $d_5$ = 1.9316 | $n_{d3}$ = 1.80610 | $v_{d3}$ = 40.95 |
| $r_6$ = ∞ | $d_6$ = 0.0000 | | |
| $r_7$ = ∞ (Stop) | $d_7$ = 0.0207 | | |
| $r_8$ = ∞ | $d_8$ = 0.2759 | $n_{d4}$ = 1.88300 | $v_{d4}$ = 40.76 |
| $r_9$ = −1.8035 | $d_9$ = 0.6899 | | |
| $r_{10}$ = −2.1647 | $d_{10}$ = 0.2139 | $n_{d5}$ = 1.84666 | $v_{d5}$ = 23.78 |
| $r_{11}$ = ∞ | $d_{11}$ = 0.6899 | $n_{d6}$ = 1.88300 | $v_{d6}$ = 40.76 |
| $r_{12}$ = −1.4993 | $d_{12}$ = 0.0690 | | |
| $r_{13}$ = 2.3066 | $d_{13}$ = 0.8251 | $n_{d7}$ = 1.51633 | $v_{d7}$ = 64.14 |
| $r_{14}$ = −1.1486 | $d_{14}$ = 0.2070 | $n_{d8}$ = 1.84666 | $v_{d8}$ = 23.78 |
| $r_{15}$ = −3.3278 | $d_{15}$ = 0.2910 | | |
| $r_{16}$ = ∞ | $d_{16}$ = 0.6899 | $n_{d9}$ = 1.51399 | $v_{d9}$ = 75.00 |
| $r_{17}$ = ∞ | $d_{17}$ = 0.0138 | $n_{d10}$ = 1.51000 | $v_{d10}$ = 63.00 |
| $r_{18}$ = ∞ | $d_{18}$ = 0.3449 | $n_{d11}$ = 1.51633 | $v_{d11}$ = 64.14 |
| $r_{19}$ = ∞ | $d_{19}$ = 0.0207 | | |
| $r_{20}$ = ∞ (Image plane) | | | |

F = 1.00
$F_{NO}$ = 5.270
Ih = 0.628
2ω (°) = 68.744
D (%) = −8.104
α (°) = 2.765

EXAMPLE 13

| | | | |
|---|---|---|---|
| $r_0$ = ∞ (Object Plane) | $d_0$ = 14.2860 | | |
| $r_1$ = ∞ | $d_1$ = 0.2721 | $n_{d1}$ = 1.76820 | $v_{d1}$ = 71.79 |
| $r_2$ = ∞ | $d_2$ = 0.2041 | | |
| $r_3$ = 2.2591 | $d_3$ = 0.2041 | $n_{d2}$ = 1.88300 | $v_{d2}$ = 40.76 |
| $r_4$ = 0.9705 | $d_4$ = 0.2313 | | |
| $r_5$ = ∞ | $d_5$ = 1.9048 | $n_{d3}$ = 1.80610 | $v_{d3}$ = 40.95 |
| $r_6$ = ∞ | $d_6$ = 0.0000 | | |
| $r_7$ = ∞ (Stop) | $d_7$ = 0.0204 | | |
| $r_8$ = ∞ | $d_8$ = 0.6803 | $n_{d4}$ = 1.88300 | $v_{d4}$ = 40.76 |
| $r_9$ = −1.6399 | $d_9$ = 0.6803 | | |
| $r_{10}$ = −2.0669 | $d_{10}$ = 0.2109 | $n_{d5}$ = 1.84666 | $v_{d5}$ = 23.78 |
| $r_{11}$ = ∞ | $d_{11}$ = 0.6803 | $n_{d6}$ = 1.88300 | $v_{d6}$ = 40.76 |
| $r_{12}$ = −1.5413 | $d_{12}$ = 0.0680 | | |
| $r_{13}$ = 2.5467 | $d_{13}$ = 0.7196 | $n_{d7}$ = 1.51742 | $v_{d7}$ = 52.43 |
| $r_{14}$ = −1.1240 | $d_{14}$ = 0.2041 | $n_{d8}$ = 1.84666 | $v_{d8}$ = 23.78 |
| $r_{15}$ = −2.9600 | $d_{15}$ = 0.2406 | | |
| $r_{16}$ = ∞ | $d_{16}$ = 0.6803 | $n_{d9}$ = 1.51399 | $v_{d9}$ = 75.00 |
| $r_{17}$ = ∞ | $d_{17}$ = 0.0136 | $n_{d10}$ = 1.51000 | $v_{d10}$ = 63.00 |
| $r_{18}$ = ∞ | $d_{18}$ = 0.3401 | $n_{d11}$ = 1.51633 | $v_{d11}$ = 64.14 |
| $r_{19}$ = ∞ | $d_{19}$ = 0.0204 | | |
| $r_{20}$ = ∞ (Image plane) | | | |

F = 1.00
$F_{NO}$ = 5.082
Ih = 0.620
2ω (°) = 68.000
D (%) = −7.702
α (°) = 0.838

EXAMPLE 14

| | | | |
|---|---|---|---|
| $r_0$ = ∞ (Object Plane) | $d_0$ = 14.0174 | | |
| $r_1$ = ∞ | $d_1$ = 0.2803 | $n_{d1}$ = 1.76820 | $v_{d1}$ = 71.79 |
| $r_2$ = ∞ | $d_2$ = 0.2002 | | |
| $r_3$ = 2.3752 | $d_3$ = 0.2002 | $n_{d2}$ = 1.88300 | $v_{d2}$ = 40.76 |
| $r_4$ = 0.6814 | $d_4$ = 0.1682 | | |
| $r_5$ = ∞ | $d_5$ = 0.0120 | | |
| $r_6$ = ∞ | $d_6$ = 2.2027 | $n_{d3}$ = 1.88300 | $v_{d3}$ = 40.76 |
| $r_7$ = ∞ (Stop) | $d_7$ = 0.0120 | | |
| $r_8$ = ∞ | $d_8$ = 0.2465 | $n_{d4}$ = 1.72916 | $v_{d4}$ = 54.68 |
| $r_9$ = −1.1787 | $d_9$ = 0.2803 | | |
| $r_{10}$ = 1.3151 | $d_{10}$ = 0.5206 | $n_{d5}$ = 1.88300 | $v_{d5}$ = 40.76 |
| $r_{11}$ = −1.9499 | $d_{11}$ = 0.2403 | $n_{d6}$ = 1.74077 | $v_{d6}$ = 27.79 |
| $r_{12}$ = 0.7230 | $d_{12}$ = 0.1802 | | |
| $r_{13}$ = ∞ | $d_{13}$ = 0.2403 | $n_{d7}$ = 1.51800 | $v_{d7}$ = 74.60 |
| $r_{14}$ = ∞ | $d_{14}$ = 0.0400 | | |
| $r_{15}$ = 3.0872 | $d_{15}$ = 0.2002 | $n_{d8}$ = 1.92286 | $v_{d8}$ = 18.90 |
| $r_{16}$ = 1.0404 | $d_{16}$ = 0.6007 | $n_{d9}$ = 1.51633 | $v_{d9}$ = 64.14 |
| $r_{17}$ = −1.0701 | $d_{17}$ = 0.1802 | | |
| $r_{18}$ = ∞ | $d_{18}$ = 0.4045 | $n_{d10}$ = 1.51633 | $v_{d10}$ = 64.14 |
| $r_{19}$ = ∞ | $d_{19}$ = 0.4005 | $n_{d11}$ = 1.61350 | $v_{d11}$ = 50.20 |
| $r_{20}$ = ∞ | $d_{20}$ = 0.0000 | | |
| $r_{21}$ = ∞ (Image plane) | | | |

F = 1.00
$F_{NO}$ = 9.075
Ih = 0.652
2ω (°) = 68.305
D (%) = −5.000
α (°) = 11.146

EXAMPLE 15

| | | | |
|---|---|---|---|
| $r_0$ = ∞ (Object Plane) | $d_0$ = 13.7201 | | |
| $r_1$ = ∞ | $d_1$ = 0.2744 | $n_{d1}$ = 1.76820 | $v_{d1}$ = 71.79 |
| $r_2$ = ∞ | $d_2$ = 0.1960 | | |

-continued

| | | | |
|---|---|---|---|
| $r_3 = 1.9900$ | $d_3 = 0.1960$ | $n_{d2} = 1.88300$ | $v_{d2} = 40.76$ |
| $r_4 = 0.6323$ | $d_4 = 0.1646$ | | |
| $r_5 = \infty$ | $d_5 = 0.0118$ | | |
| $r_6 = \infty$ | $d_6 = 2.1560$ | $n_{d3} = 1.88300$ | $v_{d3} = 40.76$ |
| $r_7 = \infty$ (Stop) | $d_7 = 0.0118$ | | |
| $r_8 = \infty$ | $d_8 = 0.2413$ | $n_{d4} = 1.72916$ | $v_{d4} = 54.68$ |
| $r_9 = -1.1327$ | $d_9 = 0.2744$ | | |
| $r_{10} = 1.3801$ | $d_{10} = 0.5096$ | $n_{d5} = 1.88300$ | $v_{d5} = 40.76$ |
| $r_{11} = -2.7705$ | $d_{11} = 0.2352$ | $n_{d6} = 1.74077$ | $v_{d6} = 27.79$ |
| $r_{12} = 0.7895$ | $d_{12} = 0.1764$ | | |
| $r_{13} = \infty$ | $d_{13} = 0.2352$ | $n_{d7} = 1.51800$ | $v_{d7} = 74.60$ |
| $r_{14} = \infty$ | $d_{14} = 0.0392$ | | |
| $r_{15} = 3.2999$ | $d_{15} = 0.1960$ | $n_{d8} = 1.92286$ | $v_{d8} = 18.90$ |
| $r_{16} = 1.5997$ | $d_{16} = 0.5880$ | $n_{d9} = 1.51633$ | $v_{d9} = 64.14$ |
| $r_{17} = -1.7023$ | $d_{17} = 0.1764$ | | |
| $r_{18} = \infty$ | $d_{18} = 0.3959$ | $n_{d10} = 1.51633$ | $v_{d10} = 64.14$ |
| $r_{19} = \infty$ | $d_{19} = 0.3920$ | $n_{d11} = 1.61350$ | $v_{d11} = 50.20$ |
| $r_{20} = \infty$ | $d_{20} = 0.0021$ | | |
| $r_{21} = \infty$ (Image plane) | | | |
| $F = 1.00$ | | | |
| $F_{NO} = 9.281$ | | | |
| $Ih = 0.639$ | | | |
| $2\omega\,(°) = 67.945$ | | | |
| $D\,(\%) = -7.009$ | | | |
| $\alpha\,(°) = 12.606$ | | | |

While the oblique-vision direction is set at 30° in the examples described above, it is understood that direct vision or an oblique vision of greater than 30° could be implemented.

Referring here to the CCD used on the image pickup plane, it is preferable to use a CCD that is minimized in terms of the decentration of its image pickup plane center and its outer housing. In many cases, endoscopes have an almost cylindrical insert. With large decentration of the CCD outer housing and image pickup plane center here, there is a large rotation locus that leads to an increase in the outer diameter of an endoscope.

According to the invention as detailed above, it is possible to provide a wide-angle endoscopic objective optical system, especially a video endoscopic objective optical system, which is minimized in distortion and field curvature and made up of only a relatively fewer spherical lenses, and an oblique-vision optical system capable of rotating in such a way as to set the desired field direction with respect to the longitudinal direction of an endoscope. The invention can further provide an optical system that is minimized in terms of the occurrence of decentration at the center of the field on a viewing plane even when an endoscope is rotated to turn the field direction to the desired field, thereby achieving an electronic endoscope most fit for viewing on TV monitors.

The endoscopic objective optical system of the invention and the imaging system that incorporates it, for instance, are embodied as follows.

(1) An endoscopic objective optical system comprising, in order from an object side thereof, a first group comprising a negative meniscus lens convex on an object side thereof, an aperture stop, a second group comprising a positive lens having a plane directed toward an object point side, a third group including at least one concave refractive surface and having a positive refracting power as a whole, and a fourth group comprising a cemented lens comprising a negative meniscus lens and a double-convex lens and having positive refracting power, so that an image is formed at an imaging device via said first group to said fourth group, characterized in that a chief ray is reflected at the convex surface of the positive lens in said second group in a direction away from an optical axis.

(2) The endoscopic objective optical system according to (1) above, characterized by satisfying the following conditions:

$$2 < f_2(n_2-1)/t_2 < 6 \quad (1)$$

$$-2.3 < f_1/F < -0.9 \quad (2)$$

$$-0.6 < PS3 < -0.2 \quad (3)$$

$$vp > 50,\ vn < 30 \quad (4)$$

$$2.3 < f_4/F \quad (5)$$

where $t_2$, $f_2$ and $n_2$ is the thickness, focal length and refractive index of the positive lens in said second group, respectively, $f_1$ is the focal length of the negative meniscus lens in said first group, F is the focal length of the whole optical system, PS3 is a Petzval's sum due to the concave refractive surface in said third group, vp and vn are the d-line Abbe constants of the positive lens and negative lens in said fourth group, and $f_4$ is the focal length of said fourth group.

(3) An imaging system comprising the endoscopic objective optical systems according to (1) or (2) above and a solid-state imaging device located on an image plane thereof, characterized in that a front unit is made up of said first group, said aperture stop and said second group, and a rear unit is made up of said third group and said fourth group, wherein said rear unit and said solid-state imaging device have a mechanically integrated structure in such a way as to be relatively rotatable with respect to said front unit with the longitudinal direction of the imaging device as an axis, and the angle of incidence of an axial marginal ray from said front unit on said rear unit is substantially parallel with said axis of rotation.

(4) An imaging system comprising an endoscopic objective optical system comprising a front unit comprising, in order from an object side thereof, a negative lens, a stop and a positive lens and a rear unit having a positive refracting power as a whole and a solid-state imaging device located on an image plane thereof, characterized in that said rear unit and said solid-state imaging device have a mechanically integrated structure in such a way as to be rotatable with respect to said front unit with the longitudinal direction of the imaging system as an axis, and the angle of incidence of an axial marginal ray from said front unit on said rear unit is substantially parallel with said axis of rotation.

(5) The imaging system according to (3) or (4) above, characterized by satisfying the following condition should be satisfied:

$$-0.3 < (f_2 - |f_1|)/F < 1.5 \quad (6)$$

where $f_1$ is the focal length of the negative lens in said front unit, $f_2$ is the focal length of the positive lens in said front unit, and F is the focal length of the whole endoscopic objective optical system.

(6) The imaging system according to any one of (3) to (5) above, characterized in that by incorporating a prism in said front unit, said endoscopic objective optical system is configured as an oblique-vision optical system.

(7) The imaging system according to any one of (3) to (6) above, characterized in that said solid-state imaging device has the center of an image pickup plane substantially in alignment with the center of an outer housing.

(8) The imaging system according to any one of (3) to (6) above, characterized in that the center of a scope outer tube is substantially in alignment with the center of the image pickup plane of the imaging device.

(9) The endoscopic objective optical system according to (1) or (2) above or the imaging system according to (3) to (8) above, characterized in that an interference filter capable of cutting off wavelengths in an infrared region is located in front of said fourth group.

(10) The endoscopic objective optical system according to (1) or (2) above or the imaging system according to (3) to (8) above, characterized in that there is an absorption type infrared cut filter located in the endoscopic objective optical system.

(11) The endoscopic objective optical system or the imaging system according to (9) above, characterized in that the angle of incidence of a chief ray on said interference filter is 25° or less.

(12) An assembling method for the endoscopic objective optical system according to any one of (1), (2) and (9)-(11) above or the imaging system according to any one of (3) to (11) above, characterized in that the asymmetry of the image plane is kept uniform by adjustment of a lens located nearest to the object side.

(13) An assembling method for the endoscopic objective optical system according to any one of (1), (2) and (9)-(11), characterized in that said front unit and said rear unit are independently assembled, and after adjustment of an optical center, they are combined with each other.

(14) An assembling method for the endoscopic objective optical system according to any one of (1), (2) and (9)-(11), characterized in that for centering of said front unit, an optical center is determined with respect to the rear unit that has an optical center previously adjusted to less than an acceptable amount.

(15) The imaging system according to any one of (3) to (11) above, characterized in that an illumination optical system located at a distal portion of an endoscope along with an objective optical system has such a as to be rotatable following the objective optical system upon directed in the field direction of the endoscope and the field direction turned by an image rotation mechanism.

(16) The endoscopic objective optical system according to any one of (1), (2) and (9)-(11) above, characterize in that the space between said front unit and said rear unit is 0.5 mm or wider.

What is claimed is:

1. An endoscopic objective optical system adapted to capture an object image to form the object image at image relay means, characterized by comprising a front unit before, and a rear unit after, a substantially afocal portion, wherein said objective optical system is relatively rotatable with said front unit and said rear unit integral with said image relay means.

2. The endoscopic objective optical system according to claim 1, characterized by satisfying the following conditions:

$$2 \leq f_2(n_2-1)/t_2 < 6 \quad (1)$$

$$-2.3 < f_1/F < -0.9 \quad (2)$$

$$-0.6 < PS3 < -0.2 \quad (3)$$

$$vp > 50,\ vn < 30 \quad (4)$$

$$2.3 \leq f_4/F \quad (5)$$

where $t_2$, $f_2$ and $n_2$ is the thickness, focal length and refractive index of the positive lens in said second group, respectively, $f_1$ is the focal length of the negative meniscus lens in said first group, F is the focal length of the whole optical system, PS3 is a Petzval's sum due to the concave refractive surface in said third group, $vp$ and $vn$ are the d-line Abbe constants of the positive lens and negative lens in said fourth group, and $f_4$ is the focal length of said fourth group.

3. An endoscopic objective optical system comprising, in order from an object side thereof, a first group comprising a negative meniscus lens convex on an object side thereof, an aperture stop, a second group comprising a positive lens having a plane directed toward an object point side, a third group including at least one concave refractive surface and having a positive refracting power as a whole, and a fourth group comprising a cemented lens comprising a negative meniscus lens and a double-convex lens and having positive refracting power, so that an image is formed at an imaging device via said first group to said fourth group, characterized in that a chief ray is reflected at the convex surface of the positive lens in said second group in a direction away from an optical axis.

4. The endoscopic objective optical system according to claim 3, characterized in that an interference filter capable of cutting off wavelengths in an infrared region is located in front of said fourth group.

5. The endoscopic objective optical system according to claim 4, characterized in that a angle of incidence of a chief ray on said interference filter is 25° or less.

6. The imaging system according to claim 5, characterized in that an illumination optical system located together with the objective optical system at an image portion at the distal end of the endoscope has a structure such that the illumination optical system is rotatable following the objective optical system when directed in a direction of the field of the endoscope with the direction of the field turned by an image rotation mechanism.

7. The endoscopic objective optical system according to claim 4, characterized in that a space between said front unit and said rear unit is 0.5 mm or wider.

8. The endoscopic objective optical system according to claim 3, characterized in that there is an absorption type infrared cut filter located in the endoscopic objective optical system.

9. An imaging system comprising an endoscopic objective optical system adapted to capture an object image to form the object image at image relay means, and a solid-state imaging device located on an image plane side thereof, characterized in that said objective optical system comprises a front unit before, and a rear unit after, a substantially afocal portion, wherein said objective optical system is relatively rotatable with said front unit and said rear unit integral with said image relay means.

10. An imaging system comprising an endoscopic objective optical system comprising, in order from an object side thereof, a first group comprising a negative meniscus lens convex on an object side thereof, an aperture stop, a second group comprising a positive lens having a plane directed toward an object point side, a third group including at least one concave refractive surface and having a positive refracting power as a whole, and a fourth group comprising a cemented lens comprising a negative meniscus lens and a double-convex lens and having positive refracting power, so that an image is formed at an imaging device via said first group to said fourth group, wherein a chief ray is reflected at the convex surface of the positive lens in said second group in a direction away from an optical axis, and a solid-state imaging device located on an image plane side of said objective optical system, characterized in that a front unit is made up of said first group, said aperture stop and said second group, and a rear unit is made up of said third group and said fourth group, wherein said rear unit and said solid-state imaging device have a mechanically integrated structure in such a way as to be relatively rotatable with respect to said front unit with the longitudinal direction of the imaging device as an axis, and the angle of incidence of an axial marginal ray from said front unit on said rear unit is substantially parallel with said axis of rotation.

11. The imaging system according to claim 10, characterized by satisfying the following condition should be satisfied:

$$-0.3<(f_2-|f_1|)/F<1.5 \quad (6)$$

where $f_1$ is the focal length of the negative lens in said front unit, $f_2$ is the focal length of the positive lens in said front unit, and F is the focal length of the whole endoscopic objective optical system.

12. The imaging system according to claim 11, characterized in that by incorporating a prism in said front unit, said endoscopic objective optical system is configured as an oblique-vision optical system.

13. The imaging system according to claim 12, characterized in that said solid-state imaging device has the center of an image pickup plane substantially in alignment with the center of an outer housing.

14. The imaging system according to claim 12, characterized in that the center of a scope outer tube is substantially in alignment with the center of the image pickup plane of the imaging device.

15. The imaging system according to claim 10, characterized in that an interference filter capable of cutting off wavelengths in an infrared region is located in front of said fourth group.

16. The imaging system according to claim 15, characterized in that the angle of incidence of a chief ray on said interference filter is 25° or less.

17. The imaging system according to claim 10, characterized in that there is an absorption type infrared cut filter located in the endoscopic objective optical system.

18. An imaging system comprising an endoscopic objective optical system comprising, in order from an object side thereof, a first group comprising a negative meniscus lens convex on an object side thereof, an aperture stop, a second group comprising a positive lens having a plane directed toward an object point side, a third group including at least one concave refractive surface and having a positive refracting power as a whole, and a fourth group comprising a cemented lens comprising a negative meniscus lens and a double-convex lens and having positive refracting power, so that an image is formed at an imaging device via said first group to said fourth group, wherein a chief ray is reflected at the convex surface of the positive lens in said second group in a direction away from an optical axis, and a solid-state imaging device located on an image plane side of said objective optical system, characterized in that a front unit is made up of said first group, said aperture stop and said second group, and a rear unit is made up of said third group and said fourth group, wherein said rear unit and said solid-state imaging device have a mechanically integrated structure in such a way as to be relatively rotatable with respect to said front unit with the longitudinal direction of the imaging device as an axis, and the angle of incidence of an axial marginal ray from said front unit on said rear unit is substantially parallel with said axis of rotation, $$2<f_2(n_2-1)/t_2<6 \quad (1)$$

$$-2.3<f_1/F<-0.9 \quad (2)$$

$$-0.6<PS3<-0.2 \quad (3)$$

$$\nu p>50, \nu n<30 \quad (4)$$

$$2.3<f_4/F \quad (5)$$

where $t_2$, $f_2$ and $n_2$ is the thickness, focal length and refractive index of the positive lens in said second group, respectively, $f_1$ is the focal length of the negative meniscus lens in said first group, F is the focal length of the whole optical system, PS3 is a Petzval's sum due to the concave refractive surface in said third group, $\nu p$ and $\nu n$ are the d-line Abbe constants of the positive lens and negative lens in said fourth group, and $f_4$ is the focal length of said fourth group.

19. An imaging system comprising an endoscopic objective optical system comprising a front unit comprising, in order from an object side thereof, a negative lens, a stop and a positive lens and a rear unit having a positive refracting power as a whole and a solid-state imaging device located on an image plane thereof, characterized in that said rear unit and said solid-state imaging device have a mechanically integrated structure in such a way as to be rotatable with respect to said front unit with the longitudinal direction of the imaging system as an axis, and the angle of incidence of an axial marginal ray from said front unit on said rear unit is substantially parallel with said axis of rotation.

20. An assembling method for an endoscopic objective optical system comprising, in order from an object side thereof, a first group comprising a negative meniscus lens convex on an object side thereof, an aperture stop, a second group comprising a positive lens having a plane directed toward an object point side, a third group including at least one concave refractive surface and having a positive refracting power as a whole, and a fourth group comprising a cemented lens comprising a negative meniscus lens and a double-convex lens and having positive refracting power, so that an image is formed at an imaging device via said first group to said fourth group, wherein a chief ray is reflected at the convex surface of the positive lens in said second group in a direction away from an optical axis, characterized in that the asymmetry of the image plane is kept uniform by adjustment of a lens located nearest to the object side.

21. An assembling method for an endoscopic objective optical system comprising, in order from an object side thereof, a first group comprising a negative meniscus lens convex on an object side thereof, an aperture stop, a second group comprising a positive lens having a plane directed toward an object point side, a third group including at least one concave refractive surface and having a positive refracting power as a whole, and a fourth group comprising a cemented lens comprising a negative meniscus lens and a double-convex lens and having positive refracting power, so that an image is formed at an imaging device via said first group to said fourth group, characterized in that a chief ray is reflected at the convex surface of the positive lens in said second group in a direction away from an optical axis, and a solid-state imaging device located on an image plane of said endoscopic objective optical system, characterized in that a front unit is made up of said first group, said aperture stop and said second group, and a rear unit is made up of said third group and said fourth group, wherein said rear unit and said solid-state imaging device have a mechanically integrated structure in such a way as to be relatively rotatable with respect to said front unit with the longitudinal direction of the imaging device as an axis, and the angle of incidence of an axial marginal ray from said front unit on said rear unit is substantially parallel with said axis of rotation, characterized in that the asymmetry of the image plane is kept uniform by adjustment of a lens located nearest to the object side.

22. An assembling method for an endoscopic objective optical system comprising, in order from an object side thereof, a first group comprising a negative meniscus lens convex on an object side thereof, an aperture stop, a second group comprising a positive lens having a plane directed toward an object point side, a third group including at least one concave refractive surface and having a positive refracting power as a whole, and a fourth group comprising a cemented lens comprising a negative meniscus lens and a double-convex lens and having positive refracting power, so that an image is formed at an imaging device via said first group to said fourth group, wherein a chief ray is reflected at the convex surface of the positive lens in said second group in a direction away from an optical axis, characterized in that said front unit and said rear unit are independently assembled, and after adjustment of an optical center, they are combined with each other.

23. An assembling method for an endoscopic objective optical system comprising, in order from an object side thereof, a first group comprising a negative meniscus lens convex on an object side thereof, an aperture stop, a second group comprising a positive lens having a plane directed toward an object point side, a third group including at least one concave refractive surface and having a positive refracting power as a whole, and a fourth group comprising a cemented lens comprising a negative meniscus lens and a double-convex lens and having positive refracting power, so that an image is formed at an imaging device via said first group to said fourth group, wherein a chief ray is reflected at the convex surface of the positive lens in said second group in a direction away from an optical axis, characterized in that for centering of said front unit, an optical center is determined with respect to the rear unit that has an optical center previously adjusted to less than an acceptable amount.

* * * * *